United States Patent
Mukumoto et al.

(10) Patent No.: US 9,265,251 B2
(45) Date of Patent: Feb. 23, 2016

(54) AGRICHEMICAL COMPOSITION AND METHOD OF PROMOTING GROWTH OF PLANT

(71) Applicant: SUMITOMO CHEMICAL COMPANY, LIMITED, Tokyo (JP)

(72) Inventors: Fujio Mukumoto, Takarazuka (JP); Hiroaki Tamaki, Takarazuka (JP)

(73) Assignee: Sumitomo Chemical Company, Limited, Tokyo (JP)

(*) Notice: Subject to any disclaimer, the term of this patent is extended or adjusted under 35 U.S.C. 154(b) by 0 days.

(21) Appl. No.: 14/045,286

(22) Filed: Oct. 3, 2013

(65) Prior Publication Data

US 2014/0135213 A1    May 15, 2014

(30) Foreign Application Priority Data

Nov. 12, 2012 (JP) ................ 2012-248098

(51) Int. Cl.
| | | |
|---|---|---|
| *A01N 43/12* | (2006.01) | |
| *A01N 37/36* | (2006.01) | |
| *A01N 37/46* | (2006.01) | |
| *A01N 37/50* | (2006.01) | |
| *A01N 43/36* | (2006.01) | |
| *A01N 43/54* | (2006.01) | |
| *A01N 43/56* | (2006.01) | |
| *A01N 43/78* | (2006.01) | |
| *A01N 43/653* | (2006.01) | |
| *A01N 47/24* | (2006.01) | |
| *A01N 57/14* | (2006.01) | |
| *A01C 1/06* | (2006.01) | |

(52) U.S. Cl.
CPC .. *A01N 43/12* (2013.01); *A01C 1/06* (2013.01)

(58) Field of Classification Search
CPC ....... A01N 43/12; A01N 37/46; A01N 43/56; A01N 43/90
USPC ................. 504/100, 289
See application file for complete search history.

(56) References Cited

U.S. PATENT DOCUMENTS 4,427,696 A * 1/1984 Hubele ............ 514/538
5,298,482 A    3/1994 Tanaka et al.

FOREIGN PATENT DOCUMENTS

| | | |
|---|---|---|
| JP | 4-342507 A | 11/1992 |
| WO | WO 2012/153860 A1 | 11/2012 |

OTHER PUBLICATIONS

Burström et al., "Root Growth Effects of Indan, Indene, and Thionaphthene Derivatives," Physiologia Plantarum, vol. 9, 1956, pp. 502-514.
Sasaki et al., "Biosynthesis, biotechnological production and applications of 5-aminolevulinic acid," Applied Microbiology and Biotechnology, vol. 58, Jan. 2002, pp. 23-29.
Tomlin, "The Pesticide Manual," Fifteenth Edition, British Crop Production Council (ISBN: 978-1-901396-18-8), 2009, pp. 584-587 and 654-655.

* cited by examiner

*Primary Examiner* — John Pak
(74) *Attorney, Agent, or Firm* — Birch, Stewart, Kolasch & Birch, LLP

(57) ABSTRACT

An agrichemical composition comprising a compound represented by the formula (1) and at least one fungicidally active compound selected from Group (A).

Group (A): metalaxyl, metalaxyl-M, benalaxyl, benalaxyl-M, pyraclostrobin, trifloxystrobin, azoxystrobin, dimoxystrobin, fluoxastrobin, kresoxim methyl, picoxystrobin, metconazole, ipconazole, tebuconazole, difenoconazole, epoxiconazole, fluquinconazole, triticonazole, triadimenol, prothioconazole, propioconazole, prochloraz, penconazole, flusilazole, diniconazole, bromuconazole, cyproconazole, triflumizole, tetraconazole, myclobutanil, bitertanol, imazalil and the like.

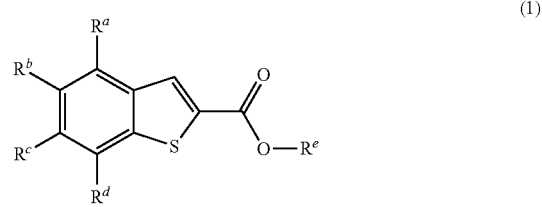

(1)

12 Claims, No Drawings

AGRICHEMICAL COMPOSITION AND METHOD OF PROMOTING GROWTH OF PLANT

TECHNICAL FIELD OF THE INVENTION

The present invention relates to an agrichemical composition and a method of promoting the growth of plants.

BACKGROUND OF THE INVENTION

Some chemical substances are known to show an effect of promoting the growth of a plant when applied to the plant. For example, aminolevulinic acid shows a growth promoting effect on a plant by application thereof.
(Nonpatent document 1) "Biosynthesis, biotechnological production and applications of 5-aminolevulinic acid" K. Sasaki et al., Applied Microbial Biotechnology 58: pp. 23-29
(Nonpatent document 2) The Pesticide Manual, Fifteenth Edition, British Crop Production Council (ISBN: 978-1-901396-18-8)

SUMMARY OF THE INVENTION

The present invention has an object of providing an excellent agrichemical composition promoting the growth of plants, and the like.

The present inventors have investigated and found that the growth of the plant is promoted by applying an agrichemical composition containing a compound represented by the following formula (1) and at least one fungicidally active compound as an active ingredient to a plant.

That is, the present invention is as described in the following [1] to [15].

[1] An agrichemical composition comprising a compound represented by the formula (1):

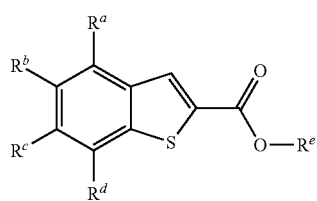

(1)

[wherein, at least one of $R^a$, $R^b$, $R^c$ and $R^d$ represents a trifluoromethyl group and others represent a hydrogen atom, and $R^e$ represents a methyl group or an ethyl group.]
and at least one fungicidally active compound selected from Group (A) (hereinafter, referred to as inventive composition):

Group (A): metalaxyl, metalaxyl-M, benalaxyl, benalaxyl-M, pyraclostrobin, trifloxystrobin, azoxystrobin, dimoxystrobin, fluoxastrobin, kresoxim methyl, picoxystrobin, N-methyl-2-[2-(2,5-dimethylphenoxy)methyl]phenyl-2-methoxyacetamide, metconazole, ipconazole, tebuconazole, difenoconazole, epoxiconazole, fluquinconazole, triticonazole, triadimenol, prothioconazole, propioconazole, prochloraz, penconazole, flusilazole, diniconazole, bromuconazole, cyproconazole, triflumizole, tetraconazole, myclobutanil, bitertanol, imazalil, simeconazole, flutriafol, sedaxane, penflufen, isopyrazam, bixafen, boscalid, fluopyram, fluxapyroxad, flutolanil, mepronil, carboxin, thifluzamide, penthiopyrad, furametpyr, isofetamid, benzovindiflupyr, probenazole, tiadinil, tricyclazole, pyroquilon, kasugamycin hydrochloride, ferimzone, isotianil, phthalide, tebufloquin, fludioxonil, ethaboxam, tolclofos-methyl, captan, thiram, iprodione, validamycin, pencycuron, mancozeb, hymexazol, compounds represented by the formula (2):

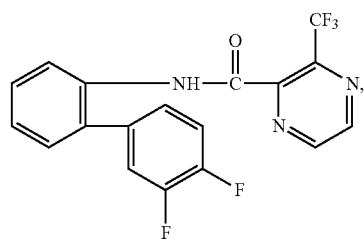

(2)

compounds represented by the formula (3):

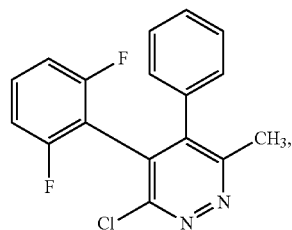

(3)

and compounds represented by the formula (4):

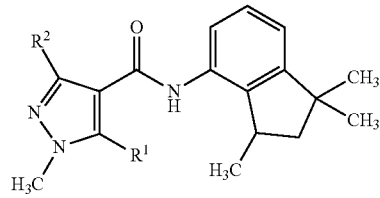

(4)

[wherein, $R^1$ represents a hydrogen atom or a methyl group and $R^2$ represents a methyl group, a difluoromethyl group or a trifluoromethyl group.].

[2] The agrichemical composition according to [1], wherein the at least one fungicidally active compound selected from Group (A) is at least one fungicidally active compound selected from Group (B):

Group (B): metalaxyl, metalaxyl-M, benalaxyl and benalaxyl-M.

[3] The agrichemical composition according to [1], wherein the at least one fungicidally active compound selected from Group (A) is at least one fungicidally active compound selected group Group (C):

Group (C): pyraclostrobin, trifloxystrobin, azoxystrobin, dimoxystrobin, fluoxastrobin, kresoxim methyl, picoxystrobin and N-methyl-2-[2-(2,5-dimethylphenoxy)methyl]phenyl-2-methoxyacetamide.

[4] The agrichemical composition according to [1], wherein the at least one fungicidally active compound selected from Group (A) is at least one fungicidally active compound selected group Group (D):

Group (D): metconazole, ipconazole, tebuconazole, difenoconazole, epoxiconazole, fluquinconazole, triticonazole, triadimenol, prothioconazole, propioconazole, prochloraz, penconazole, flusilazole, diniconazole, bromuconazole, cyproconazole, triflumizole, tetraconazole, myclobutanil, bitertanol, imazalil, simeconazole and flutriafol.

[5] The agrichemical composition according to [1], wherein the at least one fungicidally active compound selected from Group (A) is at least one fungicidally active compound selected group Group (E):

Group (E): sedaxane, penflufen, isopyrazam, bixafen, boscalid, fluopyram, fluxapyroxad, flutolanil, mepronil, carboxin, thifluzamide, penthiopyrad, furametpyr, isofetamid, benzovindiflupyr, compounds represented by the formula (2):

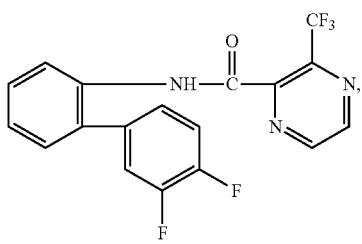

and compounds represented by the formula (3):

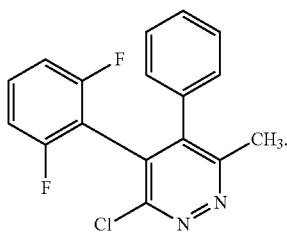

[6] The agrichemical composition according to [1], wherein the at least one fungicidally active compound selected from Group (A) is at least one fungicidally active compound selected group Group (F):

Group (F): probenazole, tiadinil, tricyclazole, pyroquilon, kasugamycin hydrochloride, ferimzone, isotianil, phthalide, tebufloquin, fludioxonil, ethaboxam, tolclofos-methyl, captan, thiram, iprodione, validamycin, pencycuron, mancozeb, hymexazol, and compounds represented by the formula (4):

(4)

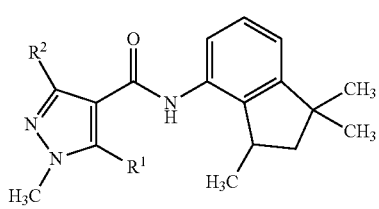

[wherein, $R^1$ represents a hydrogen atom or a methyl group and $R^2$ represents a methyl group, a difluoromethyl group or a trifluoromethyl group.].

[7] The agrichemical composition according to [1], wherein the at least one fungicidally active compound selected from Group (A) is at least one fungicidally active compound selected group Group (G):

Group (G): metalaxyl, metalaxyl-M, pyraclostrobin, trifloxystrobin, azoxystrobin, metconazole, ipconazole, tebuconazole, difenoconazole, sedaxane, penflufen, fludioxonil, ethaboxam, tolclofos-methyl, and compounds represented by the formula (4):

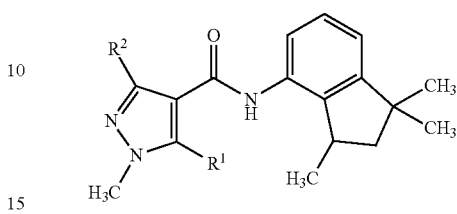

[wherein, $R^1$ represents a hydrogen atom or a methyl group and $R^2$ represents a methyl group, a difluoromethyl group or a trifluoromethyl group.].

[8] The agrichemical composition according to [1], wherein the compound represented by the formula (1) is methyl 5-(trifluoromethyl)benzo[b]thiophene-2-carboxylate.

[9] The agrichemical composition according to any one of [1] to [8], wherein the content ratio of the compound represented by the formula (1) to the at least one fungicidally active compound selected from Group (A) is 100:1 to 1:100 by weight.

[10] A method of promoting the growth of a plant, having a step of applying an effective amount of the agrichemical composition according to any one of [1] to [9] to a soil where the plant grows or the plant itself.

[11] A method of promoting the growth of a plant, having a step of adhering an effective amount of the agrichemical composition according to any one of [1] to [9] to a seed of the plant or impregnating a seed of the plant with an effective amount of the agrichemical composition according to any one of [1] to [9] and a step of sowing the plant seed.

[12] A seed treating agent comprising the agrichemical composition according to any one of [1] to [9].

[13] A plant seed impregnated with an effective amount of the agrichemical composition according to any one of [1] to [9] or comprising an effective amount of the agrichemical composition according to any one of [1] to [9] adhered.

[14] The plant seed according to [13], wherein the kind of the plant seed is a seed of corn, cotton, soybean, sugar beet, rapeseed, wheat or rice.

[15] Use of the agrichemical composition according to any one of [1] to [9], for promoting the growth of a plant.

DETAILED DESCRIPTION OF THE INVENTION

The inventive composition comprises a compound represented by the formula (1):

(1)

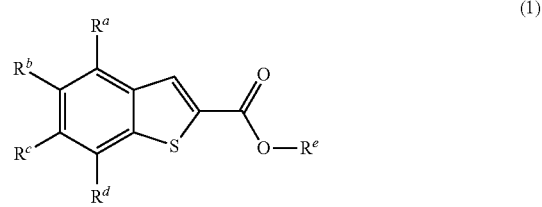

[wherein, at least one of $R^a$, $R^b$, $R^c$ and $R^d$ represents a trifluoromethyl group and others represent a hydrogen atom, and $R^e$ represents a methyl group or an ethyl group.]
(hereinafter, referred to as present condensed ring compound) and at least one fungicidally active compound selected from Group (A) (hereinafter, referred to as present fungicidally active compound).

Group (A): metalaxyl, metalaxyl-M, benalaxyl, benalaxyl-M, pyraclostrobin, trifloxystrobin, azoxystrobin, dimoxystrobin, fluoxastrobin, kresoxim methyl, picoxystrobin, N-methyl-2-[2-(2,5-dimethylphenoxy)methyl]phenyl-2-methoxyacetamide, metconazole, ipconazole, tebuconazole, difenoconazole, epoxiconazole, fluquinconazole, triticonazole, triadimenol, prothioconazole, propioconazole, prochloraz, penconazole, flusilazole, diniconazole, bromuconazole, cyproconazole, triflumizole, tetraconazole, myclobutanil, bitertanol, imazalil, simeconazole, flutriafol, sedaxane, penflufen, isopyrazam, bixafen, boscalid, fluopyram, fluxapyroxad, flutolanil, mepronil, carboxin, thifluzamide, penthiopyrad, furametpyr, isofetamid, benzovindiflupyr, probenazole, tiadinil, tricyclazole, pyroquilon, kasugamycin hydrochloride, ferimzone, isotianil, phthalide, tebufloquin, fludioxonil, ethaboxam, tolclofos-methyl, captan, thiram, iprodione, N-(1,1,3-trimethylindane-4-yl)-1-methyl-3-difluoromethylpyrazole-4-carboxylic amide, validamycin, pencycuron, mancozeb, hymexazol, compounds represented by the formula (2):

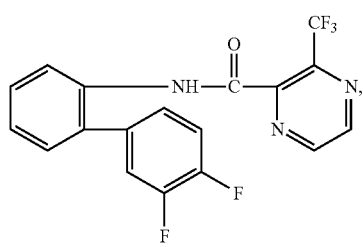 [SMILES: O=C(Nc1ccccc1-c1ccc(F)c(F)c1)c1nccnc1C(F)(F)F]

(2)

compounds represented by the formula (3):

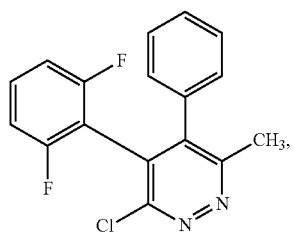 [SMILES: Cc1nnc(Cl)c(-c2c(F)cccc2F)c1-c1ccccc1]

(3)

and compounds represented by the formula (4):

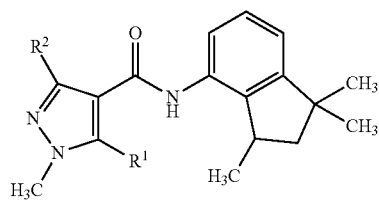

(4)

[wherein, $R^1$ represents a hydrogen atom or a methyl group and $R^2$ represents a methyl group, a difluoromethyl group or a trifluoromethyl group.].

Specific examples of the present condensed ring compound will be shown.

Specific examples of the present condensed ring compound include compounds represented by the formula (1) in which groups $R^a$, $R^b$, $R^c$, $R^d$ and $R^e$ are combined as shown in Table 1 (present condensed ring compound 1 to present condensed ring compound 8):

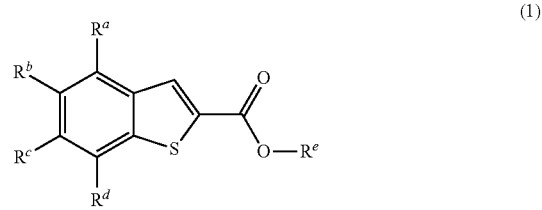

(1)

[wherein, the combination of $R^a$, $R^b$, $R^c$, $R^d$ and $R^e$ denotes any of combinations shown in [Table 1].].

TABLE 1

| Present compound | $R^a$ | $R^b$ | $R^c$ | $R^d$ | $R^e$ |
|---|---|---|---|---|---|
| Present condensed ring compound 1 | H | CF$_3$ | H | H | CH$_3$ |
| Present condensed ring compound 2 | H | H | CF$_3$ | H | CH$_3$ |
| Present condensed ring compound 3 | CF$_3$ | H | H | H | CH$_3$ |
| Present condensed ring compound 4 | H | H | H | CF$_3$ | CH$_3$ |
| Present condensed ring compound 5 | H | CF$_3$ | H | H | C$_2$H$_5$ |
| Present condensed ring compound 6 | H | H | CF$_3$ | H | C$_2$H$_5$ |
| Present condensed ring compound 7 | CF$_3$ | H | H | H | C$_2$H$_5$ |
| Present condensed ring compound 8 | H | H | H | CF$_3$ | C$_2$H$_5$ |

Next, the fungicidally active compound used as an active ingredient in the inventive composition will be specifically illustrated below.

Metalaxyl, metalaxyl-M, benalaxyl and benalaxyl-M used in the inventive composition are known compounds and described, for example, in "The Pesticide Manual—15th edition (published by BCPC); ISBN 978-1-901396-18-8", pp. 737, 739, 74 and 76. These compounds are obtained from commercially available preparations or produced by known methods.

Kresoxim methyl, azoxystrobin, pyraclostrobin, picoxystrobin, trifloxystrobin, dimoxystrobin and fluoxastrobin used in the inventive composition are known compounds and described, for example, in "The Pesticide Manual—15th edition (published by BCPC); ISBN 978-1-901396-18-8", pp. 688, 62, 971, 910, 1167, 383 and 538. These compounds are obtained from commercially available preparations or can be produced by known methods.

N-methyl-2-[2-(2,5-dimethylphenoxy)methyl]phenyl-2-methoxyacetamide used in the inventive composition (hereinafter, referred to as present fungicidally active compound 1) is a known compound and can be synthesized by a method described, for example, in International Publication No. 95/27693.

Kresoxim methyl, azoxystrobin, pyraclostrobin, picoxystrobin, trifloxystrobin, dimoxystrobin and fluoxastrobin used in the inventive composition are compounds known to show an antibacterial activity owing to a respiration inhibition action by electron transport system inhibition (Complex III inhibition) of intracellular mitochondria of a pathogenic bacterium.

Metconazole, tebuconazole, difenoconazole, triticonazole, imazalil, triadimenol, fluquinconazole, prochloraz, prothioconazole, diniconazole, tetraconazole, ipconazole, triflumizole, bitertanol, epoxiconazole, fenbuconazole, flusilazole, flutriafol, hexaconazole, myclobutanil, penconazole, propiconazole, simeconazole and triadimefon used in the inventive composition are known compounds and described, for example, in "The Pesticide Manual-15th edition (published by BCPC); ISBN 978-1-901396-18-8", pp. 749, 1072, 354, 1182, 629, 1147, 543, 928, 965, 384, 1096, 663, 1171, 116, 429, 468, 554, 560, 611, 801, 869, 952, 1033 and 1145. These compounds are obtained from commercially available preparations or produced by known methods.

Metconazole, tebuconazole, difenoconazole, triticonazole, imazalil, triadimenol, fluquinconazole, prochloraz, prothioconazole, diniconazole, tetraconazole, ipconazole, triflumizole, bitertanol, epoxiconazole, fenbuconazole, flusilazole, flutriafol, hexaconazole, myclobutanil, penconazole, propiconazole, simeconazole and triadimefon used in the inventive composition are bactericidal compounds known as a demethylation inhibiting agent (demethylation inhibitor; DMI agent).

The compounds represented by the formula (2) used in the inventive composition (hereinafter, referred to as present fungicidally active compound 2) are known and described, for example, in International Publication No. 07/07299. These compounds are obtained from commercially available preparations or produced by known methods.

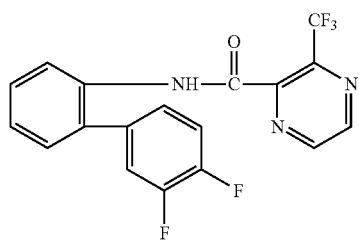

(2)

The compounds represented by the formula (3) used in the inventive composition (hereinafter, referred to as present fungicidally active compound 3) are known and described, for example, in International Publication No. 05/121104. These compounds are obtained from commercially available preparations or produced by known methods.

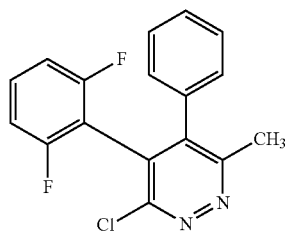

(3)

Sedaxane used in the inventive composition is a known compound represented by the formula (5) and described, for example, in International Publication No. 03/74491. This compound can be produced by a method described in this publication.

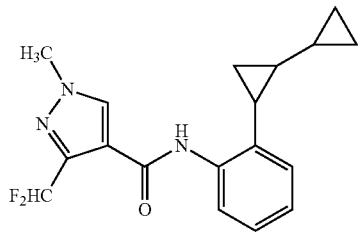

(5)

Penflufen used in the inventive composition is a known compound represented by the formula (6) and described, for example, in International Publication No. 03/10149. This compound can be produced by a method described in this publication.

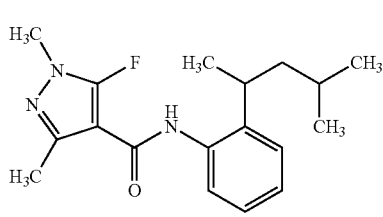

(6)

Fluxapyroxad used in the inventive composition is a known compound represented by the formula (7) and described, for example, in International Publication No. 06/087343. This compound can be produced by a method described in this publication.

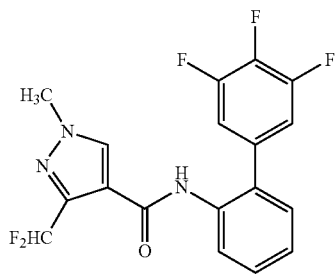

(7)

Carboxamides such as furametpyr, carboxin, flutolanil, penthiopyrad and fluopyram used in the inventive composition are all known compounds and described, for example, in "The Pesticide Manual-15th edition (published by BCPC); ISBN 978-1-901396-18-8", pp. 580, 164, 559, 877 and 535, and the like. These compounds are obtained from commercially available preparations or produced by known methods.

Isopyrazam, bixafen, boscalid, mepronil, thifluzamide and isofetamid used in the inventive composition are all known compounds and described, for example, in "The Pesticide Manual-15th edition(BCPC); ISBN 978-1-901396-18-8", pp. 676, 1080 and 1119. Bixafen or isofetamid is described, for example, in International Publication No. 03/070705 or International Publication No. 09/060734. These compounds are obtained from commercially available preparations or produced by known methods.

Benzovindiflupyr used in the inventive composition (hereinafter, referred to as present fungicidally active compound 4) is described, for example, in International Publication No.

10/049228, and obtained from commercially available preparations or produced by known methods.

Sedaxane, penflufen, isopyrazam, bixafen, boscalid, fluopyram, fluxapyroxad, flutolanil, mepronil, carboxin, thifluzamide, penthiopyrad, furametpyr and isofetamid used in the inventive composition are compounds known to show an antibacterial activity owing to a respiration inhibition action by electron transport system inhibition (Complex III inhibition) of intracellular mitochondria of a pathogenic bacterium.

Rice blast (*Pyricularia oryzae*) controlling compounds such as probenazole, tiadinil, tricyclazole, pyroquilon, kasugamycin hydrochloride and ferimzone used in the inventive composition are all known compounds and described, for example, in "The Pesticide Manual—15th edition (BCPC); ISBN 978-1-901396-18-8", pp. 927, 1134, 1163, 999, 685 and 497, and the like. These compounds are obtained from commercially available preparations or produced by known methods.

Isotianil used in the inventive composition is a known compound represented by the formula (8) and can be produced by a method described, for example, in International Publication No. 99/024413.

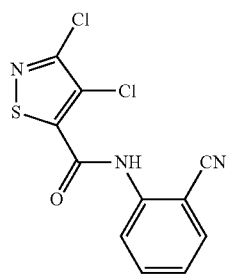

(8)

Phthalide used in the inventive composition is a known compound and described, for example, in "SHIBUYA INDEX (Index of Pesticides) 13th Edition 2008 (published by SHIBUYA INDEX RESEARCH GROUP) ISBN 9784881371435", p. 147.

Tebufloquin used in the inventive composition is a known compound represented by the formula (9) and can be produced by a method described, for example, in International Publication No. 01/092231.

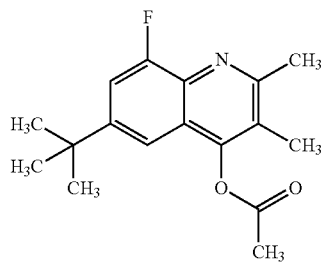

(9)

Fludioxonil, ethaboxam, tolclofosmethyl, captan, thiram, mancozeb and hymexazol used in the inventive composition are known compounds and described, for example, in "The Pesticide Manual-15th edition (published by BCPC); ISBN 978-1-901396-18-8", pp. 520, 435, 1135, 154, 546, 702 and 627. These compounds are obtained from commercially available preparations or produced by known methods.

Iprodione used in the inventive composition is a known compound and can be produced by a method described, for example, in International Publication No. 12/031061.

The compound represented by the formula (4) used in the inventive composition is a known compound and has configuration of R-form, S-form or a mixture of R-form/S-form at any proportion.

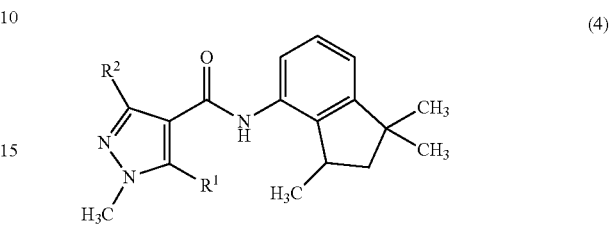

(4)

[wherein, $R^1$ and $R^2$ represent the same meaning as described above.]

The compound represented by the formula (4) in which $R^1$ is a hydrogen atom and $R^2$ is difluoromethyl (hereinafter, referred to as present fungicidally active compound 5) and the like can be produced by a method described, for example, in International Publication No. 2011/162397.

Rice sheath blight (*Thanatephorus cucumeris*) controlling compounds such as pencycuron and validamycin used in the inventive composition are all known compounds and described, for example, in "The Pesticide Manual-15th edition (published by BCPC); ISBN 978-1-901396-18-8", pp. 871 and 1187, and the like. These compounds are obtained from commercially available preparations or produced by known methods.

The content proportion of the present condensed ring compound and the present fungicidally active compound in the inventive composition is not particularly restricted, however, the proportion of the present fungicidally active compound is usually 2 to 10000000 parts by weight, preferably 10 to 100000 parts by weight with respect to 1000 parts by weight of the present condensed ring compound.

The inventive composition includes, for example, the following embodiments.

A composition containing any one of the present condensed ring compounds 1 to 8 and metalaxyl;

A composition containing any one of the present condensed ring compounds 1 to 8 and metalaxyl-M;

A composition containing any one of the present condensed ring compounds 1 to 8 and benalaxyl;

A composition containing any one of the present condensed ring compounds 1 to 8 and benalaxyl-M;

A composition containing any one of the present condensed ring compounds 1 to 8 and pyraclostrobin;

A composition containing any one of the present condensed ring compounds 1 to 8 and trifloxystrobin;

A composition containing any one of the present condensed ring compounds 1 to 8 and azoxystrobin;

A composition containing any one of the present condensed ring compounds 1 to 8 and dimoxystrobin;

A composition containing any one of the present condensed ring compounds 1 to 8 and fluoxastrobin;

A composition containing any one of the present condensed ring compounds 1 to 8 and kresoxim methyl;

A composition containing any one of the present condensed ring compounds 1 to 8 and picoxystrobin;

A composition containing any one of the present condensed ring compounds 1 to 8 and the present fungicidally active compound 1;
A composition containing any one of the present condensed ring compounds 1 to 8 and metconazole;
A composition containing any one of the present condensed ring compounds 1 to 8 and ipconazole;
A composition containing any one of the present condensed ring compounds 1 to 8 and tebuconazole;
A composition containing any one of the present condensed ring compounds 1 to 8 and difenoconazole;
A composition containing any one of the present condensed ring compounds 1 to 8 and epoxiconazole;
A composition containing any one of the present condensed ring compounds 1 to 8 and fluquinconazole;
A composition containing any one of the present condensed ring compounds 1 to 8 and triticonazole;
A composition containing any one of the present condensed ring compounds 1 to 8 and triadimenol;
A composition containing any one of the present condensed ring compounds 1 to 8 and prothioconazole;
A composition containing any one of the present condensed ring compounds 1 to 8 and propioconazole;
A composition containing any one of the present condensed ring compounds 1 to 8 and prochloraz;
A composition containing any one of the present condensed ring compounds 1 to 8 and penconazole;
A composition containing any one of the present condensed ring compounds 1 to 8 and flusilazole;
A composition containing any one of the present condensed ring compounds 1 to 8 and diniconazole;
A composition containing any one of the present condensed ring compounds 1 to 8 and bromuconazole;
A composition containing any one of the present condensed ring compounds 1 to 8 and cyproconazole;
A composition containing any one of the present condensed ring compounds 1 to 8 and triflumizole;
A composition containing any one of the present condensed ring compounds 1 to 8 and tetraconazole;
A composition containing any one of the present condensed ring compounds 1 to 8 and myclobutanil;
A composition containing any one of the present condensed ring compounds 1 to 8 and bitertanol;
A composition containing any one of the present condensed ring compounds 1 to 8 and imazalil;
A composition containing any one of the present condensed ring compounds 1 to 8 and simeconazole;
A composition containing any one of the present condensed ring compounds 1 to 8 and flutriafol;
A composition containing any one of the present condensed ring compounds 1 to 8 and sedaxane;
A composition containing any one of the present condensed ring compounds 1 to 8 and penflufen;
A composition containing any one of the present condensed ring compounds 1 to 8 and isopyrazam;
A composition containing any one of the present condensed ring compounds 1 to 8 and bixafen;
A composition containing any one of the present condensed ring compounds 1 to 8 and boscalid;
A composition containing any one of the present condensed ring compounds 1 to 8 and fluopyram;
A composition containing any one of the present condensed ring compounds 1 to 8 and fluxapyroxad;
A composition containing any one of the present condensed ring compounds 1 to 8 and flutolanil;
A composition containing any one of the present condensed ring compounds 1 to 8 and mepronil;
A composition containing any one of the present condensed ring compounds 1 to 8 and carboxin;
A composition containing any one of the present condensed ring compounds 1 to 8 and thifluzamide;
A composition containing any one of the present condensed ring compounds 1 to 8 and penthiopyrad;
A composition containing any one of the present condensed ring compounds 1 to 8 and furametpyr;
A composition containing any one of the present condensed ring compounds 1 to 8 and isofetamid;
A composition containing any one of the present condensed ring compounds 1 to 8 and the present fungicidally active compound 2;
A composition containing any one of the present condensed ring compounds 1 to 8 and probenazole;
A composition containing any one of the present condensed ring compounds 1 to 8 and tiadinil;
A composition containing any one of the present condensed ring compounds 1 to 8 and tricyclazole;
A composition containing any one of the present condensed ring compounds 1 to 8 and pyroquilon;
A composition containing any one of the present condensed ring compounds 1 to 8 and kasugamycin hydrochloride;
A composition containing any one of the present condensed ring compounds 1 to 8 and ferimzone;
A composition containing any one of the present condensed ring compounds 1 to 8 and isotianil;
A composition containing any one of the present condensed ring compounds 1 to 8 and phthalide;
A composition containing any one of the present condensed ring compounds 1 to 8 and tebufloquin;
A composition containing any one of the present condensed ring compounds 1 to 8 and fludioxonil;
A composition containing any one of the present condensed ring compounds 1 to 8 and ethaboxam;
A composition containing any one of the present condensed ring compounds 1 to 8 and tolclofos-methyl;
A composition containing any one of the present condensed ring compounds 1 to 8 and captan;
A composition containing any one of the present condensed ring compounds 1 to 8 and thiram;
A composition containing any one of the present condensed ring compounds 1 to 8 and mancozeb;
A composition containing any one of the present condensed ring compounds 1 to 8 and hymexazol;
A composition containing any one of the present condensed ring compounds 1 to 8 and iprodione;
A composition containing any one of the present condensed ring compounds 1 to 8 and the present fungicidally active compound 3;
A composition containing any one of the present condensed ring compounds 1 to 8 and the present fungicidally active compound 4;
A composition containing any one of the present condensed ring compounds 1 to 8 and the present fungicidally active compound 5;
A composition containing any one of the present condensed ring compounds 1 to 8 and validamycin;
A composition containing any one of the present condensed ring compounds 1 to 8 and pencycuron.
A composition containing any one of the present condensed ring compounds 1 to 8 and metalaxyl at a weight ratio of 0.01/1 to 100/1;
A composition containing any one of the present condensed ring compounds 1 to 8 and metalaxyl-M at a weight ratio of 0.01/1 to 100/1;

A composition containing any one of the present condensed ring compounds 1 to 8 and benalaxyl at a weight ratio of 0.01/1 to 100/1;
A composition containing any one of the present condensed ring compounds 1 to 8 and benalaxyl-M at a weight ratio of 0.01/1 to 100/1;
A composition containing any one of the present condensed ring compounds 1 to 8 and pyraclostrobin at a weight ratio of 0.01/1 to 100/1;
A composition containing any one of the present condensed ring compounds 1 to 8 and trifloxystrobin at a weight ratio of 0.01/1 to 100/1;
A composition containing any one of the present condensed ring compounds 1 to 8 and azoxystrobin at a weight ratio of 0.01/1 to 100/1;
A composition containing any one of the present condensed ring compounds 1 to 8 and dimoxystrobin at a weight ratio of 0.01/1 to 100/1;
A composition containing any one of the present condensed ring compounds 1 to 8 and fluoxastrobin at a weight ratio of 0.01/1 to 100/1;
A composition containing any one of the present condensed ring compounds 1 to 8 and kresoxim methyl at a weight ratio of 0.01/1 to 100/1;
A composition containing any one of the present condensed ring compounds 1 to 8 and picoxystrobin at a weight ratio of 0.01/1 to 100/1;
A composition containing any one of the present condensed ring compounds 1 to 8 and the present fungicidally active compound 1 at a weight ratio of 0.01/1 to 100/1;
A composition containing any one of the present condensed ring compounds 1 to 8 and metconazole at a weight ratio of 0.01/1 to 100/1;
A composition containing any one of the present condensed ring compounds 1 to 8 and ipconazole at a weight ratio of 0.01/1 to 100/1;
A composition containing any one of the present condensed ring compounds 1 to 8 and tebuconazole at a weight ratio of 0.01/1 to 100/1;
A composition containing any one of the present condensed ring compounds 1 to 8 and difenoconazole at a weight ratio of 0.01/1 to 100/1;
A composition containing any one of the present condensed ring compounds 1 to 8 and epoxiconazole at a weight ratio of 0.01/1 to 100/1;
A composition containing any one of the present condensed ring compounds 1 to 8 and fluquinconazole at a weight ratio of 0.01/1 to 100/1;
A composition containing any one of the present condensed ring compounds 1 to 8 and triticonazole at a weight ratio of 0.01/1 to 100/1;
A composition containing any one of the present condensed ring compounds 1 to 8 and triadimenol at a weight ratio of 0.01/1 to 100/1;
A composition containing any one of the present condensed ring compounds 1 to 8 and prothioconazole at a weight ratio of 0.01/1 to 100/1;
A composition containing any one of the present condensed ring compounds 1 to 8 and propioconazole at a weight ratio of 0.01/1 to 100/1;
A composition containing any one of the present condensed ring compounds 1 to 8 and prochloraz at a weight ratio of 0.01/1 to 100/1;
A composition containing any one of the present condensed ring compounds 1 to 8 and penconazole at a weight ratio of 0.01/1 to 100/1;
A composition containing any one of the present condensed ring compounds 1 to 8 and flusilazole at a weight ratio of 0.01/1 to 100/1;
A composition containing any one of the present condensed ring compounds 1 to 8 and diniconazole at a weight ratio of 0.01/1 to 100/1;
A composition containing any one of the present condensed ring compounds 1 to 8 and bromuconazole at a weight ratio of 0.01/1 to 100/1;
A composition containing any one of the present condensed ring compounds 1 to 8 and cyproconazole at a weight ratio of 0.01/1 to 100/1;
A composition containing any one of the present condensed ring compounds 1 to 8 and triflumizole at a weight ratio of 0.01/1 to 100/1;
A composition containing any one of the present condensed ring compounds 1 to 8 and tetraconazole at a weight ratio of 0.01/1 to 100/1;
A composition containing any one of the present condensed ring compounds 1 to 8 and myclobutanil at a weight ratio of 0.01/1 to 100/1;
A composition containing any one of the present condensed ring compounds 1 to 8 and bitertanol at a weight ratio of 0.01/1 to 100/1;
A composition containing any one of the present condensed ring compounds 1 to 8 and imazalil at a weight ratio of 0.01/1 to 100/1;
A composition containing any one of the present condensed ring compounds 1 to 8 and simeconazole at a weight ratio of 0.01/1 to 100/1;
A composition containing any one of the present condensed ring compounds 1 to 8 and flutriafol at a weight ratio of 0.01/1 to 100/1;
A composition containing any one of the present condensed ring compounds 1 to 8 and sedaxane at a weight ratio of 0.01/1 to 100/1;
A composition containing any one of the present condensed ring compounds 1 to 8 and penflufen at a weight ratio of 0.01/1 to 100/1;
A composition containing any one of the present condensed ring compounds 1 to 8 and isopyrazam at a weight ratio of 0.01/1 to 100/1;
A composition containing any one of the present condensed ring compounds 1 to 8 and bixafen at a weight ratio of 0.01/1 to 100/1;
A composition containing any one of the present condensed ring compounds 1 to 8 and boscalid at a weight ratio of 0.01/1 to 100/1;
A composition containing any one of the present condensed ring compounds 1 to 8 and fluopyram at a weight ratio of 0.01/1 to 100/1;
A composition containing any one of the present condensed ring compounds 1 to 8 and fluxapyroxad at a weight ratio of 0.01/1 to 100/1;
A composition containing any one of the present condensed ring compounds 1 to 8 and flutolanil at a weight ratio of 0.01/1 to 100/1;
A composition containing any one of the present condensed ring compounds 1 to 8 and mepronil at a weight ratio of 0.01/1 to 100/1;
A composition containing any one of the present condensed ring compounds 1 to 8 and carboxin at a weight ratio of 0.01/1 to 100/1;
A composition containing any one of the present condensed ring compounds 1 to 8 and thifluzamide at a weight ratio of 0.01/1 to 100/1;

A composition containing any one of the present condensed ring compounds 1 to 8 and penthiopyrad at a weight ratio of 0.01/1 to 100/1;
A composition containing any one of the present condensed ring compounds 1 to 8 and furametpyr at a weight ratio of 0.01/1 to 100/1;
A composition containing any one of the present condensed ring compounds 1 to 8 and isofetamid at a weight ratio of 0.01/1 to 100/1;
A composition containing any one of the present condensed ring compounds 1 to 8 and the present fungicidally active compound 2 at a weight ratio of 0.01/1 to 100/1;
A composition containing any one of the present condensed ring compounds 1 to 8 and probenazole at a weight ratio of 0.01/1 to 100/1;
A composition containing any one of the present condensed ring compounds 1 to 8 and tiadinil at a weight ratio of 0.01/1 to 100/1;
A composition containing any one of the present condensed ring compounds 1 to 8 and tricyclazole at a weight ratio of 0.01/1 to 100/1;
A composition containing any one of the present condensed ring compounds 1 to 8 and pyroquilon at a weight ratio of 0.01/1 to 100/1;
A composition containing any one of the present condensed ring compounds 1 to 8 and kasugamycin hydrochloride at a weight ratio of 0.01/1 to 100/1;
A composition containing any one of the present condensed ring compounds 1 to 8 and ferimzone at a weight ratio of 0.01/1 to 100/1;
A composition containing any one of the present condensed ring compounds 1 to 8 and isotianil at a weight ratio of 0.01/1 to 100/1;
A composition containing any one of the present condensed ring compounds 1 to 8 and phthalide at a weight ratio of 0.01/1 to 100/1;
A composition containing any one of the present condensed ring compounds 1 to 8 and tebufloquin at a weight ratio of 0.01/1 to 100/1;
A composition containing any one of the present condensed ring compounds 1 to 8 and fludioxonil at a weight ratio of 0.01/1 to 100/1;
A composition containing any one of the present condensed ring compounds 1 to 8 and ethaboxam at a weight ratio of 0.01/1 to 100/1;
A composition containing any one of the present condensed ring compounds 1 to 8 and tolclofos-methyl at a weight ratio of 0.01/1 to 100/1;
A composition containing any one of the present condensed ring compounds 1 to 8 and captan at a weight ratio of 0.01/1 to 100/1;
A composition containing any one of the present condensed ring compounds 1 to 8 and thiram at a weight ratio of 0.01/1 to 100/1;
A composition containing any one of the present condensed ring compounds 1 to 8 and mancozeb at a weight ratio of 0.01/1 to 100/1;
A composition containing any one of the present condensed ring compounds 1 to 8 and hymexazol at a weight ratio of 0.01/1 to 100/1;
A composition containing any one of the present condensed ring compounds 1 to 8 and iprodione at a weight ratio of 0.01/1 to 100/1;
A composition containing any one of the present condensed ring compounds 1 to 8 and the present fungicidally active compound 3 at a weight ratio of 0.01/1 to 100/1;
A composition containing any one of the present condensed ring compounds 1 to 8 and the present fungicidally active compound 4 at a weight ratio of 0.01/1 to 100/1;
A composition containing any one of the present condensed ring compounds 1 to 8 and the present fungicidally active compound 5 at a weight ratio of 0.01/1 to 100/1;
A composition containing any one of the present condensed ring compounds 1 to 8 and validamycin at a weight ratio of 0.01/1 to 100/1;
A composition containing any one of the present condensed ring compounds 1 to 8 and pencycuron at a weight ratio of 0.01/1 to 100/1.

The inventive composition may be a mixture itself consisting of the present condensed ring compound and the present fungicidally active compound, however, in usual cases, the present condensed ring compound, the present fungicidally active compound and an inert carrier are mixed, and if necessary, a surfactant and other auxiliary agents for formulation are added, and the mixture is formulated into an oil solution, an emulsifiable concentrate, a flowable formulation, a wettable powder, a granular wettable powder, a dust formulation, a granule formulation or the like.

The above-described formulated inventive composition can be used as it is as an agrichemical composition, or other inert components can be added to the composition before use as an agrichemical composition.

The total amount of the present condensed ring compound and the present fungicidally active compound in the inventive composition is usually in the range of 0.1 to 99% by weight, preferably 0.2 to 90% by weight, more preferably 1 to 80% by weight.

Examples of the solid carrier used in formulation include fine powders or granules made of minerals such as kaolin clay, attapulgite clay, bentonite, montmorillonite, acidic white clay, pyrophylite, talc, diatomaceous earth, calicite and the like, natural organic substances such as corncob flour, walnut shell flour and the like, synthetic organic substances such as urea and the like, salts such as calcium carbonate, ammonium sulfate and the like, synthetic inorganic substances such as synthetic hydrated silicon oxide, and the like, and examples of the liquid carrier used in formulation include aromatic hydrocarbons such as xylene, alkylbenzene, methyl naphthalene and the like, alcohols such as 2-propanol, ethylene glycol, propylene glycol, ethylene glycol monoethyl ether and the like, ketones such as acetone, cyclohexanone, isophorone and the like, vegetable oils such as soybean oil, cotton seed oil and the like, petroleum-based aliphatic hydrocarbons, esters, dimethyl sulfoxide, acetonitrile, and water.

Examples of the surfactant include anionic surfactants such as alkyl sulfate ester salts, alkylaryl sulfonates, dialkyl sulfosuccinates, polyoxyethylene alkylaryl ether phosphate ester salts, ligninsulfonates, naphthalene sulfonate formaldehyde polycondensates and the like, nonionic surfactants such as polyoxyethylene alkylaryl ethers, polyoxyethylene alkylpolyoxypropylene block copolymers, sorbitan fatty acid esters and the like, and cationic surfactants such as alkyl trimethyl ammonium salts and the like.

Examples of the other auxiliary agents for formulation include water-soluble polymers such as polyvinyl alcohol, polyvinyl pyrrolidone and the like, polysaccharides such as gum arabic, alginic acid and a salt thereof, CMC (carboxymethyl cellulose), xanthane gum and the like, inorganic substances such as aluminum magnesium silicate, alumina-sol and the like, preservatives, colorants, and stabilizers such as PAP (isopropyl acid phosphate), BHT and the like.

In the present invention, "promoting the growth of a plant" (hereinafter, referred to as "growth promotion" in some cases) refers to an increase in the seedling establishment rate, an increase in the number of healthy leaves, an increase in the plant length, an increase in the plant body weight, an increase in the leaf area, an greening in the leaf color, an increase in the number or weight of seeds or fruits, an increase in the number of set flowers or fruits, an increase in the growth of roots, an increase in the chlorophyll fluorescence, and an increase in the transpiration capacity.

Growth promotion can be quantified using the following parameters:

(1) Seedling Establishment Rate

Seeds of plants are sown, for example, in the soil, on a filter paper, on an agar culture medium, on sand or the like, and then allowed to undergo cultivation for a given period of time, and the proportion of germinated and grown seedlings is examined.

(2) Number or Ratio of Healthy Leaves

With respect to each of plants, the number of healthy leaves is counted and the total number of healthy leaves is examined. Alternatively, the ratio of the number of healthy leaves to the number of all leaves of plants is examined.

(3) Plant Length

With respect to each of plants, the length from the base of the stem of the aerial part to the branches and leaves at the tip is measured.

(4) Plant Body Weight

The aerial part of each of plants is cut and the weight is measured to determine the fresh weight of plants. Alternatively, the cut sample is dried and the weight is measured to determine a dry weight of plants.

(5) Leaf Area

A photograph of plants is taken by a digital camera and the area of a green portion in the photograph is determined by image analysis software, for example, Win ROOF (manufactured by MITANI CORPORATION), to obtain the leaf area of plants.

(6) Leaf Color

After sampling leaves of plants, the chlorophyll content is measured using a chlorophyll gauge (for example, SPAD-502, manufactured by Konica Minolta Holdings, Inc.) to determine the leaf color. The plants are photographed with a digital camera and the green area of plant leaves in the photograph is measured by extracting color for quantification using image analysis software, such as Win ROOF (manufactured by MITANI CORPORATION).

(7) Number or Weight of Seeds or Fruits

Plants are grown until they reach fructification or ripening of seeds or fruits, and then the number of fruits per plant is counted or the total weight of fruits per plant is measured. After cultivating plants until seeds undergo ripening, elements constituting the yield such as the number of panicles, ripening rate and thousand kernel weight are examined.

(8) Flower Setting Rate, Fruit Setting Rate, Seed Setting Rate and Seed Filling Rate After cultivating plants until they bear fruits, the number of flower setting and the number of fruit setting are counted to calculate the fruit setting rate % (number of fruit setting/number of flower setting×100). After seeds are ripe, the numbers of set seeds and filled seeds are counted to calculate the seed setting rate (%) (number of set seeds/number of set flowers×100) and the seed filling rate (%) (number of filled seeds/number of set seeds×100).

(9) Growth of Roots

Plants are cultivated in the soil or in hydroponics, then, the length of roots is measured or the roots are cut and the fresh weight thereof is measured.

(10) Chlorophyll Fluorescence Yield

Using a pulse-modulated chlorophyll fluorescence measurement apparatus (for example, IMAGING-PAM, manufactured by WALZ), the chlorophyll fluorescence value of plants (Fv/Fm) is measured to obtain the chlorophyll fluorescence yield.

(11) Transpiration Capacity

At each growth stage of plants, transpiration of water from the surface of leaves is measured using a porometer (for example, AP4, manufactured by Delta-T Devices Ltd.).

In the inventive method, when the inventive composition is applied to a plant, the plant may be an entire plant or part thereof (stem and leaf, shoot, flower, fruit, panicle, seed, bulb, tuber, root and the like), further, may be at any of various stages of the plant growth (the germination period, including preseeding time, seeding time, and the period before and after the seedling emergence after sowing; the vegetative growth period, including the nursery period, the time of seedling transplantation, the time of planting or nursing cuttings and the growth period after field planting; the reproductive growth period, including the periods before, during and after flowering, immediately before heading or the heading period; and the harvest period, including a period before the expected harvest date, a period before the expected ripening date and the time of initiation of fruit coloration). As used herein, the term bulb refers to a scaly bulb, corm, rhizome, root tuber and rhizophore. The seedlings may include seedling, cuttings and the like. When applied to a plant, the inventive composition is applied once or several times.

When the inventive composition is applied to a soil where a plant grows in the inventive method, an effective amount of the inventive composition is applied to the plant cultivation area. When applied to the plant cultivation area, the inventive composition is applied once or several times.

Specific examples of the application method in the inventive method include application to foliage, floral organs or panicles of plants, such as foliage spraying, application to a soil (cultivation areas) before or after planting, application to seeds, such as seed sterilization, seed soaking, seed coating and the like, application to seedlings, application to bulbs such as seed potato, and the like.

Specific examples of the method of application to foliage, floral organs or panicles in the inventive method include methods of applying to the surface of plants, such as foliage spraying, trunk spraying and the like. Also, examples thereof include spray treatment of floral organs or entire plants in the flowering stage including before, during and after flowering. Further, examples thereof include spray treatment of panicles or entire plants in the heading stage, for crop plants and the like.

Examples of the method of application to a soil in the inventive method include spraying onto the soil, soil incorporation, and perfusion of a chemical liquid into the soil (irrigation of chemical liquid, soil injection, and dripping of chemical liquid). Examples of the place to be treated include planting hole, furrow, around a planting hole, around a furrow, entire surface of cultivation lands, the parts between the soil and the plant, area between roots, area beneath the trunk, main furrow, growing soil, seedling raising box, seedling raising tray, seedbed and the like. Examples of the treating period include before seeding, at the time of seeding, immediately after seeding, raising period, before settled planting, at the time of settled planting, growing period after settled planting, and the like. In the above-described soil treatment, the present condensed ring compound and the present fungicidally active compound may be simultaneously applied a plant, or a solid fertilizer such as a paste fertilizer containing the inventive compound may be applied to the soil. Also, the inventive composition may be mixed in an irrigation liquid, and, examples thereof include injecting to irrigation facilities (irrigation tube, irrigation pipe, sprinkler, etc.), mixing into the flooding liquid between furrows, mixing into a hydroponic medium and the like. Alternatively, an irrigation liquid may be mixed with the inventive composition in advance and, for example, used for treatment by an appropriate irrigating method including the irrigation method mentioned above and the other methods such as sprinkling, flooding and the like.

The method of applying to seeds in the inventive method refers to a process for adhering the inventive composition to seeds, bulbs and the like of plants of interest or impregnating seeds, bulbs and the like of plants of interest with the inventive composition, and specific examples thereof include a spraying treatment by which a suspension of the inventive composition is atomized to be sprayed onto the surface of seeds or bulbs, a smear treatment by which the inventive composition in the form of a wettable powder, an emulsifiable concentrate, a flowable formulation or the like is applied, directly or after being added with a small amount of water, onto seeds or bulbs, a soaking treatment in which seeds are soaked into a solution of the inventive composition for a certain period of time, a film coating treatment, and a pellet coating treatment.

Examples of the method of application to seedlings in the inventive method include spraying treatment of spraying to the entire seedlings a diluted liquid having a proper concentration of active ingredients prepared by diluting the inventive composition with water, immersing treatment of immersing seedlings in the diluted liquid, and coating treatment of adhering the inventive composition formulated into a dust formulation to the entire seedlings. Examples of the method of application to the soil before or after sowing seedlings include a method of spraying a diluted liquid having a proper concentration of active ingredients prepared by diluting the inventive composition with water onto seedlings or the soil around seedlings after sowing seedlings, and a method of spraying the inventive composition formulated into a solid formulation such as a granule onto soil around seedlings after sowing seedlings.

The inventive composition may be mixed with a hydroponic medium in hydroponics, and may also be used as one of culture medium components in tissue culture. When the hydroponic treatment method in the inventive method is used for hydroponics, the inventive composition can be dissolved or suspended in a conventionally used culture medium for hydroponics such as horticulture tests at a concentration of active ingredients within a range of 0.001 ppm to 1000 ppm. When the inventive composition is used at the time of tissue culture or cell culture, it can be dissolved or suspended in a conventionally used culture medium for plant tissue culture, such as a Murashige-and-Skoog culture medium or a conventionally used culture medium for hydroponics, such as a Hoagland medium, at a concentration of active ingredients within a range of 0.001 ppm to 1000 ppm. In this case, in accordance with a usual method, saccharides as a carbon source, various phytohormones and the like can be appropriately added.

When the inventive composition is applied to a solid where a plant grows or a plant itself, the application amount can vary according to the kind of plants to be treated, formulation form, application period, meteorological conditions and the like, but is usually within a range of 0.1 g to 10000 g, preferably 1 to 1000 g, in terms of an active ingredient amount, per 10000 m$^2$. When the inventive composition is incorporated into the entire soil, the application amount is usually within a range of 0.1 to 10 000 g, preferably 1 to 1000 g, in terms of an active ingredient amount, per 10000 m$^2$.

An emulsifiable concentrate, a wettable powder, a flowable formulation, a microcapsule and the like are usually applied by spraying after dilution with water. In this case, the concentration of the active ingredient is usually within a range of 0.1 ppm to 10000 ppm, preferably 1 ppm to 1000 ppm, in the inventive composition. A dust formulation, a granule formulation and the like are usually used for application as they are without dilution.

In application to seeds, the amount of the inventive composition per 100 kg of seeds is usually 0.01 to 1000 g, preferably 0.1 to 100 g, in terms of the active ingredient amount of the present condensed ring compound.

The plants to which the inventive method can be applied include the following plants.

Crops: corn, rice, wheat, barley, rye, oat, sorghum, cotton, soybean, peanut, buckwheat, sugar beet, oilseed rape, sunflower, sugar cane, tobacco, hop, etc.;

Vegetables: *solanaceous* vegetables (eggplant, tomato, potato, pepper, sweet pepper, etc.), *cucurbitaceous* vegetables (cucumber, pumpkin, zucchini, water melon, melon, oriental melon, etc.), *cruciferous* vegetables (Japanese radish, turnip, horseradish, kohlrabi, Chinese cabbage, cabbage, rape, leaf mustard, broccoli, cauliflower, etc.), *asteraceous* vegetables (burdock, crown daisy, artichoke, lettuce, etc.), *liliaceous* vegetables (green onion, onion, garlic, asparagus, etc.), *apiaceous* vegetables (carrot, parsley, celery, parsnip, etc.), *chenopodiaceous* vegetables (spinach, chard, etc.), *Labiatae* vegetables (Japanese basil, mint, basil, etc.), *leguminous* vegetables (pea, common bean, azuki bean, broad bean, chikbean, etc.), strawberry, sweet potato, Japanese yam, taro, *Amorphophallus konjac*, ginger, okra, etc.;

Fruits: *pomaceous* fruits (apple, pear, Japanese pear, Chinese quince, quince, etc.), stone fleshy fruits (peach, plum, nectarine, *Prunus mume*, cherry fruit, apricot, prune, etc.), *citrus* fruits (*Citrus unshiu*, orange, lemon, rime, grapefruit, etc.), nuts (chestnuts, walnuts, hazelnuts, almond, pistachio, cashew nuts, macadamia nuts, etc.), berries (blueberry, cranberry, blackberry, raspberry, etc.), grape, persimmon, olive, Japanese plum, banana, coffee, date palm, coconuts, oil palm, etc.; Trees other than fruit trees: tea, mulberry, flowering trees (*Rhododendron indicum, camellia, hydrangea, sasanqua, skimmia*, cherry, tulip tree, crape myrtle, orange *osmanthus*, etc.), roadside trees (ash tree, birch, dogwood, *eucalyptus, ginkgo biloba*, lilac, maple, oak, poplar, redbud, *liquidambar*, sycamore, *zelkova*, Japanese arborvitae, fir, hemlock fir, juniper, pine, spruce, yew, elm, chestnut, etc.), *Viburnum awabuki, Podocarpus macrophyllus*, cedar, cypress, croton, Japanese spindle, Japanese *photinia*, etc.;

Grasses: *Zoysia* grasses (*Z. japonica, Z. pacifica*, etc.), bermudagrasses (Bermuda grass, etc.), bent grasses (redtop, creeping bent, colonial bent, etc.), bluegrasses (Kentucky bluegrass, rough bluegrass, etc.), fescues (tall fescue, Chewing's fescue, creeping red fescue, etc.), ryegrasses (darnel, rye grass, etc.), orchard grass, timothy grass, etc.; and Other plants: ornamental flowers (rose, carnation, *chrysanthemum, eustoma, gypsophila, gerbera*, marigold, *salvia, petunia, verbena*, tulip, aster, gentian, lily, pansy, cyclamen, orchid, lily of the valley, lavender, stock, ornamental cabbage, *primula*, poinsettia, *gladiolus*, cattleya, daisy, cymbidium, *begonia*, etc.), biofuel plants (Jatropha, safflower, camellias, switchgrass, *miscanthus*, reed canarygrass, giant cane, kenaf, cassava, willow, etc.), ornamental plants, etc.

Examples of the plants applicable to the present invention include, preferably, tea, apple, pear, grape, cherry fruit, peach, nectarine, persimmon, Japanese plum, plum, soybean, lettuce, cabbage, tomato, eggplant, cucumber, watermelon, melon, common bean, pea, azuki bean, grass, oilseed rape, strawberry, almond, corn, sorghum, broad bean, Chinese cabbage, potato, peanut, rice, wheat, taro, *Amorphophallus konjac*, Japanese yam, Japanese radish, turnip, parsley, oriental melon, okra, ginger, lemon, orange, grapefruit, lime, blueberry, chestnut, hop, cotton, sugar beet and basil, more preferably, rice, wheat, corn, soybean, oilseed rape, cotton, sugar beet and the like.

The above-described "plants" may be plants obtained by introducing herbicide tolerance conferring genes, pest-selective toxin producing genes, disease resistance conferring genes, or abiotic stress reducing genes thereinto by genetic engineering techniques or hybridization breeding method, or stack varieties obtained by introducing a plurality of these genes thereinto.

The inventive composition may be further applied to a seed or a plant simultaneously with a pesticide, a fungicide, a biomaterial, and a safener against a certain herbicide, and the like. The usable biomaterial includes, specifically, *Bacillus firmus, Bacillus subtilis, Bacillus thuringiensis* var. *aizawai, Bacillus thuringiensis* var. *Kurstaki, Bacillus thuringiensis* var. *tenebriosis*, and the like In the inventive method, the plant to which the inventive composition is applied may be a plant which has been or is to be exposed to an abiotic stress. Such "abiotic stress" may be quantified as "intensity of stress" according to the equation shown below, and its value may be 105 to 200, preferably 110 to 180, more preferably 120 to 160.

"Intensity of stress"=100דany one of the plant phenotypes in plants not being exposed to an abiotic stress factor"/"the one of the plant phenotypes in plants being exposed to the abiotic stress factor"    Equation (I):

As used herein, an "abiotic stress" is defined as a stress that leads to growth inhibition of a plant, when the plant is exposed to an abiotic stress factor, such as temperature stress, i.e., high- or low-temperature stress, water stress, i.e., drought stress or excessive moisture stress, or salt stress, due to reduced physiological function of the cells of the plant and deterioration of the physiological state of the plant. The high-temperature stress refers to a stress that plants experience when they are exposed to a temperature exceeding the suitable temperature for their growth or germination, specifically, the high-temperature stress may be caused under conditions in which the average growth temperature is 25° C. or higher, more harshly 30° C. or higher, and even more harshly 35° C. or higher in the environment in which the plants are cultivated. The low-temperature stress refers to a stress that plants experience when they are exposed to a temperature lower than the suitable temperature for their growth or germination, specifically, the low-temperature stress may be caused under conditions in which the average growth temperature is 15° C. or lower, more harshly 10° C. or lower, and even more harshly 5° C. or lower in the environment in which the plants are cultivated. The drought stress refers to a stress that plants experience when they are exposed to a moisture environment that retards their growth by preventing water absorption due to a reduction in the water content of the soil caused by a shortage of rainfall or irrigation, specifically, the drought stress may be caused under conditions in which the water content in the soil in which the plants are grown is 15% by weight or less, more harshly 10% by weight or less, and even more harshly 7.5% by weight or less, although these values may vary depending on the type of the soil, or in which the pF value of the soil in which the plants are grown is 2.3 or more, more harshly 2.7 or more, and even more harshly 3.0 or more, although these values may vary depending on the type of the soil. The excessive moisture stress refers to a stress that plants experience when they are exposed, to a moisture environment in which the water content in the soil is excessively high, so that the growth of the plants is inhibited, specifically, the excessive moisture stress may be caused under conditions in which the water content in the soil in which the plants are grown is 30% by weight or more, more harshly 40% by weight or more, and even more harshly 50% by weight or more, although these values may vary depending on the type of the soil, or in which the pF value of the soil in which the plants are grown is 1.7 or less, more harshly 1.0 or less, and even more harshly 0.3 or less, although these values may vary depending on the type of the soil. The pF value of soil can be determined according to the principle described in "Method for pF Value Measurement" on pages 61 and 62 of "Dojyo, Shokubutsu Eiyo, Kankyo Jiten (Encyclopedia of Soil, Plant Nutrition and Environment)" (TAIYOSHA Co., Ltd., 1994, Matsuzaka et al.). The salt stress refers to a stress that plants experience when they are exposed to an environment that retards their growth by preventing water absorption due to an increase in the osmotic pressure caused by accumulation of salts contained in the soil or hydroponic solution in which the plants are cultivated, specifically, the salt stress may be caused under conditions in which the osmotic pressure potential due to the salts contained in the soil or hydroponic solution is 0.2 MPa (NaCl concentration of 2400 ppm) or higher, harshly 0.25 MPa or higher, and more harshly 0.30 MPa or higher. The osmotic pressure in soil can be calculated according to Raoult's equation shown below, by diluting the soil with water and analyzing the supernatant for salt concentration:

$\pi$ (atm)=$cRT$    Raoult's Equation:

R=0.082 (L-atm/mol-K)
T=Absolute temperature (K)
c=Ion molar concentration (mol/L)
1 atm=0.1 MPa

EXAMPLES

The present invention will be illustrated further in detail by production examples, formulation examples, application examples and test examples below, but the present invention is not limited only to the following examples. In the following examples, parts are by weight unless otherwise stated.

Production Example 1

A mixture of 5.0 g of 2-fluoro-5-(trifluoromethyl)benzaldehyde, 3.3 g of methyl thioglycolate, 4.0 g of potassium carbonate and 50 ml of DMF was stirred at 60° C. for 2 hours. The reaction mixture was cooled down to room temperature. To the reaction mixture was added water, and the mixture was extracted with tert-butyl methyl ether three times. The combined organic layers were washed with water and saturated saline, and dried over magnesium sulfate, then, concentrated under reduced pressure. The residue was recrystallized from methanol, to obtain 6.3 g of methyl 5-(trifluoromethyl)benzo[b]thiophene-2-carboxylate (present condensed ring compound 1).
[Present Condensed Ring Compound 1]
$^1$H-NMR (CDCl$_3$) δ: 8.16 (s, 1H), 8.13 (s, 1H), 7.99 (d, J=8.7 Hz, 1H), 7.67 (d, J=8.7 Hz, 1H), 3.98 (s, 3H)

Production Example 2

A mixture of 1.11 g of 2-fluoro-4-(trifluoromethyl)benzaldehyde, 739 mg of methyl thioglycolate, 1.3 g of potassium carbonate and 20 ml of DMF was stirred at 140° C. for 2 hours. The reaction mixture was cooled down to room temperature. To the reaction mixture was added water, and the mixture was extracted with tert-butyl methyl ether three times. The combined organic layers were washed with water and saturated saline, and dried over magnesium sulfate, then, concentrated under reduced pressure, to obtain 848 mg of methyl 6-(trifluoromethyl)benzo[b]thiophene-2carboxylate (present condensed ring compound 2).
[Present Condensed Ring Compound 2]
$^1$H-NMR (CDCl$_3$) δ: 8.17 (s, 1H), 8.11 (s, 1H), 7.99 (m, 1H), 7.64 (m, 1H), 3.98 (s, 3H)

Production Example 3

A mixture of 1.00 g of 2-fluoro-6-(trifluoromethyl)benzaldehyde, 633 mg of methyl thioglycolate, 1.21 g of potassium carbonate and 15 ml of DMF was stirred at 130° C. for 2 hours. The reaction mixture was cooled down to room temperature. To the reaction mixture was added water, and the mixture was extracted with tert-butyl methyl ether three times. The combined organic layers were washed with water and saturated saline, and dried over magnesium sulfate, then, concentrated under reduced pressure, to obtain 480 mg of methyl 4-(trifluoromethyl)benzo[b]thiophene-2-carboxylate (present condensed ring compound 3).
[Present Condensed Ring Compound 3]
$^1$H-NMR (CDCl$_3$) δ: 8.27 (s, 1H), 8.06 (m, 1H), 7.72 (m, 1H), 7.54 (m, 1H), 3.98 (s, 3H)

Production Example 4

A mixture of 600 mg of 2-fluoro-3-(trifluoromethyl)benzaldehyde, 398 mg of methyl thioglycolate, 694 mg of potassium carbonate and 10 ml of DMF was stirred at 140° C. for 2 hours. The reaction mixture was cooled down to room temperature. To the reaction mixture was added water, and the mixture was washed with tert-butyl methyl ether three times. To the aqueous layer was added hydrochloric acid, then, the mixture was extracted with tert-butyl methyl ether three times. The combined organic layers were washed with water and saturated saline, and dried over magnesium sulfate, then, concentrated under reduced pressure. To the residue was added water to cause deposition of a solid which was then collected by filtration, and dried under reduced pressure. To the resultant solid were added 20 ml of methanol and 0.31 ml of oxalyl chloride, and the mixture was stirred at 80° C. for 2 hours. The reaction mixture was cooled down to room temperature, then, concentrated under reduced pressure. The residue was subjected to silica gel column chromatography, to obtain 338 mg of methyl 7-(trifluoromethyl)benzo[b]thiophene-2-carboxylate (present condensed ring compound 4).
[Present Condensed Ring Compound 4]
$^1$H-NMR (CDCl$_3$) δ: 8.13 (s, 1H), 8.06 (m, 1H), 7.77 (m, 1H), 7.52 (m, 1H), 3.97 (s, 3H)

Production Example 5

Ethyl 5-(trifluoromethyl)benzo[b]thiophene-2-carboxylate (present condensed ring compound 5) is obtained by a process according to Production Example 1 excepting that ethyl thioglycolate is used instead of methyl thioglycolate.

Production Example 6

Ethyl 6-(trifluoromethyl)benzo[b]thiophene-2-carboxylate (present condensed ring compound 6) is obtained by a process according to Production Example 1 excepting that 2-fluoro-4-(trifluoromethyl)benzaldehyde is used instead of 2-fluoro-5-(trifluoromethyl)benzaldehyde and ethyl thioglycolate is used instead of methyl thioglycolate.

Production Example 7

Ethyl 4-(trifluoromethyl)benzo[b]thiophene-2-carboxylate (present condensed ring compound 7) is obtained by a process according to Production Example 1 excepting that 2-fluoro-6-(trifluoromethyl)benzaldehyde is used instead of 2-fluoro-5-(trifluoromethyl)benzaldehyde and ethyl thioglycolate is used instead of methyl thioglycolate.

Production Example 8

Ethyl 7-(trifluoromethyl)benzo[b]thiophene-2-carboxylate (present condensed ring compound 8) is obtained by a process according to Production Example 1 excepting that 2-fluoro-3-(trifluoromethyl)benzaldehyde is used instead of 2-fluoro-5-(trifluoromethyl)benzaldehyde and ethyl thioglycolate is used instead of methyl thioglycolate.

Next, formulation examples of the inventive composition will be shown.

Formulation Example 1

Twenty parts (20 parts) of any one of the present compounds 1 to 8 and 2 parts of metalaxyl-M are added into a mixture prepared by mixing 4 parts of sodium lauryl sulfate, 2 parts of calcium lignin sulfonate, 20 parts of a synthetic hydrated silicon oxide fine powder and 52 parts of diatomaceous earth, and these are mixed by well stirring to obtain each 20% wettable powder.

Formulation Example 2

Twenty parts (20 parts) of any one of the present compounds 1 to 8 and 2 parts of pyraclostrobin are added into a mixture prepared by mixing 4 parts of sodium lauryl sulfate, 2 parts of calcium lignin sulfonate, 20 parts of a synthetic hydrated silicon oxide fine powder and 52 parts of diatomaceous earth, and these are mixed by well stirring to obtain each 20% wettable powder.

Formulation Example 3

Twenty parts (20 parts) of any one of the present compounds 1 to 8 and 2 parts of trifloxystrobin are added into a mixture prepared by mixing 4 parts of sodium lauryl sulfate, 2 parts of calcium lignin sulfonate, 20 parts of a synthetic hydrated silicon oxide fine powder and 52 parts of diatomaceous earth, and these are mixed by well stirring to obtain each 20% wettable powder.

Formulation Example 4

Twenty parts (20 parts) of any one of the present compounds 1 to 8 and 2 parts of azoxystrobin are added into a mixture prepared by mixing 4 parts of sodium lauryl sulfate, 2 parts of calcium lignin sulfonate, 20 parts of a synthetic hydrated silicon oxide fine powder and 52 parts of diatomaceous earth, and these are mixed by well stirring to obtain each 20% wettable powder.

Formulation Example 5

Twenty parts (20 parts) of any one of the present compounds 1 to 8 and 2 parts of metconazole are added into a mixture prepared by mixing 4 parts of sodium lauryl sulfate, 2 parts of calcium lignin sulfonate, 20 parts of a synthetic hydrated silicon oxide fine powder and 52 parts of diatomaceous earth, and these are mixed by well stirring to obtain each 20% wettable powder.

Formulation Example 6

Twenty parts (20 parts) of any one of the present compounds 1 to 8 and 2 parts of ipconazole are added into a mixture prepared by mixing 4 parts of sodium lauryl sulfate, 2 parts of calcium lignin sulfonate, 20 parts of a synthetic hydrated silicon oxide fine powder and 52 parts of diatomaceous earth, and these are mixed by well stirring to obtain each 20% wettable powder.

Formulation Example 7

Twenty parts (20 parts) of any one of the present compounds 1 to 8 and 2 parts of tebuconazole are added into a mixture prepared by mixing 4 parts of sodium lauryl sulfate, 2 parts of calcium lignin sulfonate, 20 parts of a synthetic hydrated silicon oxide fine powder and 52 parts of diatomaceous earth, and these are mixed by well stirring to obtain each 20% wettable powder.

Formulation Example 8

Twenty parts (20 parts) of any one of the present compounds 1 to 8 and 2 parts of difenoconazole are added into a mixture prepared by mixing 4 parts of sodium lauryl sulfate, 2 parts of calcium lignin sulfonate, 20 parts of a synthetic hydrated silicon oxide fine powder and 52 parts of diatomaceous earth, and these are mixed by well stirring to obtain each 20% wettable powder.

Formulation Example 9

Twenty parts (20 parts) of any one of the present compounds 1 to 8 and 2 parts of sedaxane are added into a mixture prepared by mixing 4 parts of sodium lauryl sulfate, 2 parts of calcium lignin sulfonate, 20 parts of a synthetic hydrated silicon oxide fine powder and 52 parts of diatomaceous earth, and these are mixed by well stirring to obtain each 20% wettable powder.

Formulation Example 10

Twenty parts (20 parts) of any one of the present compounds 1 to 8 and 2 parts of penflufen are added into a mixture prepared by mixing 4 parts of sodium lauryl sulfate, 2 parts of calcium lignin sulfonate, 20 parts of a synthetic hydrated silicon oxide fine powder and 52 parts of diatomaceous earth, and these are mixed by well stirring to obtain each 20% wettable powder.

Formulation Example 11

Twenty parts (20 parts) of any one of the present compounds 1 to 8 and 2 parts of fludioxonil are added into a mixture prepared by mixing 4 parts of sodium lauryl sulfate, 2 parts of calcium lignin sulfonate, 20 parts of a synthetic hydrated silicon oxide fine powder and 52 parts of diatomaceous earth, and these are mixed by well stirring to obtain each 20% wettable powder.

Formulation Example 12

Twenty parts (20 parts) of any one of the present compounds 1 to 8 and 2 parts of ethaboxam are added into a mixture prepared by mixing 4 parts of sodium lauryl sulfate, 2 parts of calcium lignin sulfonate, 20 parts of a synthetic hydrated silicon oxide fine powder and 52 parts of diatomaceous earth, and these are mixed by well stirring to obtain each 20% wettable powder.

Formulation Example 13

Twenty parts (20 parts) of any one of the present compounds 1 to 8 and 2 parts of tolclofos-methyl are added into a mixture prepared by mixing 4 parts of sodium lauryl sulfate, 2 parts of calcium lignin sulfonate, 20 parts of a synthetic hydrated silicon oxide fine powder and 52 parts of diatomaceous earth, and these are mixed by well stirring to obtain each 20% wettable powder.

Formulation Example 14

Twenty parts (20 parts) of any one of the present compounds 1 to 8 and 2 parts of the present fungicidally active compound 5 are added into a mixture prepared by mixing 4 parts of sodium lauryl sulfate, 2 parts of calcium lignin sulfonate, 20 parts of a synthetic hydrated silicon oxide fine powder and 52 parts of diatomaceous earth, and these are mixed by well stirring to obtain each 20% wettable powder.

Formulation Example 15

To 2 parts of any one of the present compounds 1 to 8 and 0.2 parts of metalaxyl are added 1 part of a synthetic hydrated silicon oxide fine powder, 2 parts of calcium lignin sulfonate, 30 parts of bentonite and 64.8 parts of kaolin clay, and these are mixed by sufficiently stirring. After that, to these mixtures is added an appropriate amount of water, the mixtures are further stirred, granulated by a granulator, and dried under ventilation to obtain each 2% granule formulation.

Formulation Example 16

To 2 parts of any one of the present compounds 1 to 8 and 0.2 parts of metalaxyl-M are added 1 part of a synthetic hydrated silicon oxide fine powder, 2 parts of calcium lignin sulfonate, 30 parts of bentonite and 64.8 parts of kaolin clay, and these are mixed by sufficiently stirring. After that, to these mixtures is added an appropriate amount of water, the mixtures are further stirred, granulated by a granulator, and dried under ventilation to obtain each 2% granule formulation.

Formulation Example 17

To 2 parts of any one of the present compounds 1 to 8 and 0.2 parts of pyraclostrobin are added 1 part of a synthetic hydrated silicon oxide fine powder, 2 parts of calcium lignin sulfonate, 30 parts of bentonite and 64.8 parts of kaolin clay, and these are mixed by sufficiently stirring. After that, to these mixtures is added an appropriate amount of water, the mixtures are further stirred, granulated by a granulator, and dried under ventilation to obtain each 2% granule formulation.

Formulation Example 18

To 2 parts of any one of the present compounds 1 to 8 and 0.2 parts of trifloxystrobin are added 1 part of a synthetic hydrated silicon oxide fine powder, 2 parts of calcium lignin sulfonate, 30 parts of bentonite and 64.8 parts of kaolin clay, and these are mixed by sufficiently stirring. After that, to these mixtures is added an appropriate amount of water, the mixtures are further stirred, granulated by a granulator, and dried under ventilation to obtain each 2% granule formulation.

Formulation Example 19

To 2 parts of any one of the present compounds 1 to 8 and 0.2 parts of azoxystrobin are added 1 part of a synthetic hydrated silicon oxide fine powder, 2 parts of calcium lignin sulfonate, 30 parts of bentonite and 64.8 parts of kaolin clay, and these are mixed by sufficiently stirring. After that, to these mixtures is added an appropriate amount of water, the mixtures are further stirred, granulated by a granulator, and dried under ventilation to obtain each 2% granule formulation.

Formulation Example 20

To 2 parts of any one of the present compounds 1 to 8 and 0.2 parts of metconazole are added 1 part of a synthetic hydrated silicon oxide fine powder, 2 parts of calcium lignin sulfonate, 30 parts of bentonite and 64.8 parts of kaolin clay, and these are mixed by sufficiently stirring. After that, to these mixtures is added an appropriate amount of water, the mixtures are further stirred, granulated by a granulator, and dried under ventilation to obtain each 2% granule formulation.

Formulation Example 21

To 2 parts of any one of the present compounds 1 to 8 and 0.2 parts of ipconazole are added 1 part of a synthetic hydrated silicon oxide fine powder, 2 parts of calcium lignin sulfonate, 30 parts of bentonite and 64.8 parts of kaolin clay, and these are mixed by sufficiently stirring. After that, to these mixtures is added an appropriate amount of water, the mixtures are further stirred, granulated by a granulator, and dried under ventilation to obtain each 2% granule formulation.

Formulation Example 22

To 2 parts of any one of the present compounds 1 to 8 and 0.2 parts of tebuconazole are added 1 part of a synthetic hydrated silicon oxide fine powder, 2 parts of calcium lignin sulfonate, 30 parts of bentonite and 64.8 parts of kaolin clay, and these are mixed by sufficiently stirring. After that, to these mixtures is added an appropriate amount of water, the mixtures are further stirred, granulated by a granulator, and dried under ventilation to obtain each 2% granule formulation.

Formulation Example 23

To 2 parts of any one of the present compounds 1 to 8 and 0.2 parts of difenoconazole are added 1 part of a synthetic hydrated silicon oxide fine powder, 2 parts of calcium lignin sulfonate, 30 parts of bentonite and 64.8 parts of kaolin clay, and these are mixed by sufficiently stirring. After that, to these mixtures is added an appropriate amount of water, the mixtures are further stirred, granulated by a granulator, and dried under ventilation to obtain each 2% granule formulation.

Formulation Example 24

To 2 parts of any one of the present compounds 1 to 8 and 0.2 parts of sedaxane are added 1 part of a synthetic hydrated silicon oxide fine powder, 2 parts of calcium lignin sulfonate, 30 parts of bentonite and 64.8 parts of kaolin clay, and these are mixed by sufficiently stirring. After that, to these mixtures is added an appropriate amount of water, the mixtures are further stirred, granulated by a granulator, and dried under ventilation to obtain each 2% granule formulation.

Formulation Example 25

To 2 parts of any one of the present compounds 1 to 8 and 0.2 parts of penflufen are added 1 part of a synthetic hydrated silicon oxide fine powder, 2 parts of calcium lignin sulfonate, 30 parts of bentonite and 64.8 parts of kaolin clay, and these are mixed by sufficiently stirring. After that, to these mixtures is added an appropriate amount of water, the mixtures are further stirred, granulated by a granulator, and dried under ventilation to obtain each 2% granule formulation.

Formulation Example 26

To 2 parts of any one of the present compounds 1 to 8 and 0.2 parts of fludioxonil are added 1 part of a synthetic hydrated silicon oxide fine powder, 2 parts of calcium lignin sulfonate, 30 parts of bentonite and 64.8 parts of kaolin clay, and these are mixed by sufficiently stirring. After that, to these mixtures is added an appropriate amount of water, the mixtures are further stirred, granulated by a granulator, and dried under ventilation to obtain each 2% granule formulation.

Formulation Example 27

To 2 parts of any one of the present compounds 1 to 8 and 0.2 parts of ethaboxam are added 1 part of a synthetic hydrated silicon oxide fine powder, 2 parts of calcium lignin sulfonate, 30 parts of bentonite and 64.8 parts of kaolin clay, and these are mixed by sufficiently stirring. After that, to these mixtures is added an appropriate amount of water, the mixtures are further stirred, granulated by a granulator, and dried under ventilation to obtain each 2% granule formulation.

Formulation Example 28

To 2 parts of any one of the present compounds 1 to 8 and 0.2 parts of tolclofos-methyl are added 1 part of a synthetic hydrated silicon oxide fine powder, 2 parts of calcium lignin sulfonate, 30 parts of bentonite and 64.8 parts of kaolin clay, and these are mixed by sufficiently stirring. After that, to these mixtures is added an appropriate amount of water, the mixtures are further stirred, granulated by a granulator, and dried under ventilation to obtain each 2% granule formulation.

Formulation Example 29

To 2 parts of any one of the present compounds 1 to 8 and 0.2 parts of the present fungicidally active compound 5 are added 1 part of a synthetic hydrated silicon oxide fine powder, 2 parts of calcium lignin sulfonate, 30 parts of bentonite and 64.8 parts of kaolin clay, and these are mixed by sufficiently stirring. After that, to these mixtures is added an appropriate amount of water, the mixtures are further stirred, granulated by a granulator, and dried under ventilation to obtain each 2% granule formulation.

Formulation Example 30

One part (1 part) of any one of the present compounds 1 to 8 and 0.1 part of metalaxyl are dissolved in an appropriate amount of acetone, to this are added 5 parts of a synthetic hydrated silicon oxide fine powder, 0.3 parts of PAP and 93.6 parts of Fubasami clay, these are mixed by sufficiently stirring, and acetone is removed by distillation to obtain each 1% dust formulation.

Formulation Example 31

One part (1 part) of any one of the present compounds 1 to 8 and 0.1 part of metalaxyl-M are dissolved in an appropriate amount of acetone, to this are added 5 parts of a synthetic hydrated silicon oxide fine powder, 0.3 parts of PAP and 93.6 parts of Fubasami clay, these are mixed by sufficiently stirring, and acetone is removed by distillation to obtain each 1% dust formulation.

Formulation Example 32

One part (1 part) of any one of the present compounds 1 to 8 and 0.1 part of pyraclostrobin are dissolved in an appropriate amount of acetone, to this are added 5 parts of a synthetic hydrated silicon oxide fine powder, 0.3 parts of PAP and 93.6 parts of Fubasami clay, these are mixed by sufficiently stirring, and acetone is removed by distillation to obtain each 1% dust formulation.

Formulation Example 33

One part (1 part) of any one of the present compounds 1 to 8 and 0.1 part of trifloxystrobin are dissolved in an appropriate amount of acetone, to this are added 5 parts of a synthetic hydrated silicon oxide fine powder, 0.3 parts of PAP and 93.6 parts of Fubasami clay, these are mixed by sufficiently stirring, and acetone is removed by distillation to obtain each 1% dust formulation.

Formulation Example 34

One part (1 part) of any one of the present compounds 1 to 8 and 0.1 part of azoxystrobin are dissolved in an appropriate amount of acetone, to this are added 5 parts of a synthetic hydrated silicon oxide fine powder, 0.3 parts of PAP and 93.6 parts of Fubasami clay, these are mixed by sufficiently stirring, and acetone is removed by distillation to obtain each 1% dust formulation.

Formulation Example 35

One part (1 part) of any one of the present compounds 1 to 8 and 0.1 part of metconazole are dissolved in an appropriate amount of acetone, to this are added 5 parts of a synthetic hydrated silicon oxide fine powder, 0.3 parts of PAP and 93.6 parts of Fubasami clay, these are mixed by sufficiently stirring, and acetone is removed by distillation to obtain each 1% dust formulation.

Formulation Example 36

One part (1 part) of any one of the present compounds 1 to 8 and 0.1 part of ipconazole are dissolved in an appropriate amount of acetone, to this are added 5 parts of a synthetic hydrated silicon oxide fine powder, 0.3 parts of PAP and 93.6 parts of Fubasami clay, these are mixed by sufficiently stirring, and acetone is removed by distillation to obtain each 1% dust formulation.

Formulation Example 37

One part (1 part) of any one of the present compounds 1 to 8 and 0.1 part of tebuconazole are dissolved in an appropriate amount of acetone, to this are added 5 parts of a synthetic hydrated silicon oxide fine powder, 0.3 parts of PAP and 93.6 parts of Fubasami clay, these are mixed by sufficiently stirring, and acetone is removed by distillation to obtain each 1% dust formulation.

Formulation Example 38

One part (1 part) of any one of the present compounds 1 to 8 and 0.1 part of difenoconazole are dissolved in an appropriate amount of acetone, to this are added 5 parts of a synthetic hydrated silicon oxide fine powder, 0.3 parts of PAP and 93.6 parts of Fubasami clay, these are mixed by sufficiently stirring, and acetone is removed by distillation to obtain each 1% dust formulation.

Formulation Example 39

One part (1 part) of any one of the present compounds 1 to 8 and 0.1 part of sedaxane are dissolved in an appropriate amount of acetone, to this are added 5 parts of a synthetic hydrated silicon oxide fine powder, 0.3 parts of PAP and 93.6 parts of Fubasami clay, these are mixed by sufficiently stirring, and acetone is removed by distillation to obtain each 1% dust formulation.

Formulation Example 40

One part (1 part) of any one of the present compounds 1 to 8 and 0.1 part of penflufen are dissolved in an appropriate amount of acetone, to this are added 5 parts of a synthetic hydrated silicon oxide fine powder, 0.3 parts of PAP and 93.6 parts of Fubasami clay, these are mixed by sufficiently stirring, and acetone is removed by distillation to obtain each 1% dust formulation.

Formulation Example 41

One part (1 part) of any one of the present compounds 1 to 8 and 0.1 part of fludioxonil are dissolved in an appropriate amount of acetone, to this are added 5 parts of a synthetic hydrated silicon oxide fine powder, 0.3 parts of PAP and 93.6 parts of Fubasami clay, these are mixed by sufficiently stirring, and acetone is removed by distillation to obtain each 1% dust formulation.

Formulation Example 42

One part (1 part) of any one of the present compounds 1 to 8 and 0.1 part of ethaboxam are dissolved in an appropriate amount of acetone, to this are added 5 parts of a synthetic hydrated silicon oxide fine powder, 0.3 parts of PAP and 93.6 parts of Fubasami clay, these are mixed by sufficiently stirring, and acetone is removed by distillation to obtain each 1% dust formulation.

Formulation Example 43

One part (1 part) of any one of the present compounds 1 to 8 and 0.1 part of tolclofos-methyl are dissolved in an appropriate amount of acetone, to this are added 5 parts of a synthetic hydrated silicon oxide fine powder, 0.3 parts of PAP and 93.6 parts of Fubasami clay, these are mixed by sufficiently stirring, and acetone is removed by distillation to obtain each 1% dust formulation.

Formulation Example 44

One part (1 part) of any one of the present compounds 1 to 8 and 0.1 part of the present fungicidally active compound 5 are dissolved in an appropriate amount of acetone, to this are added 5 parts of a synthetic hydrated silicon oxide fine powder, 0.3 parts of PAP and 93.6 parts of Fubasami clay, these are mixed by sufficiently stirring, and acetone is removed by distillation to obtain each 1% dust formulation.

Formulation Example 45

Ten parts (10 parts) of any one of the present compounds 1 to 8 and 1 part of metalaxyl; 17.5 parts of a polyoxyethylene alkyl ether sulfate ammonium salt; 17.5 parts of white carbon; and 54 parts of water are mixed and finely pulverized by a wet pulverization method to obtain each 10% flowable formulation.

Formulation Example 46

Ten parts (10 parts) of any one of the present compounds 1 to 8 and 1 part of metalaxyl-M; 17.5 parts of a polyoxyethylene alkyl ether sulfate ammonium salt; 17.5 parts of white carbon; and 54 parts of water are mixed and finely pulverized by a wet pulverization method to obtain each 10% flowable formulation.

Formulation Example 47

Ten parts (10 parts) of any one of the present compounds 1 to 8 and 1 part of pyraclostrobin; 17.5 parts of a polyoxyethylene alkyl ether sulfate ammonium salt; 17.5 parts of white carbon; and 54 parts of water are mixed and finely pulverized by a wet pulverization method to obtain each 10% flowable formulation.

Formulation Example 48

Ten parts (10 parts) of any one of the present compounds 1 to 8 and 1 part of trifloxystrobin; 17.5 parts of a polyoxyethylene alkyl ether sulfate ammonium salt; 17.5 parts of white carbon; and 54 parts of water are mixed and finely pulverized by a wet pulverization method to obtain each 10% flowable formulation.

Formulation Example 49

Ten parts (10 parts) of any one of the present compounds 1 to 8 and 1 part of azoxystrobin; 17.5 parts of a polyoxyethylene alkyl ether sulfate ammonium salt; 17.5 parts of white carbon; and 54 parts of water are mixed and finely pulverized by a wet pulverization method to obtain each 10% flowable formulation.

Formulation Example 50

Ten parts (10 parts) of any one of the present compounds 1 to 8 and 1 part of metconazole; 17.5 parts of a polyoxyethylene alkyl ether sulfate ammonium salt; 17.5 parts of white carbon; and 54 parts of water are mixed and finely pulverized by a wet pulverization method to obtain each 10% flowable formulation.

Formulation Example 51

Ten parts (10 parts) of any one of the present compounds 1 to 8 and 1 part of ipconazole; 17.5 parts of a polyoxyethylene alkyl ether sulfate ammonium salt; 17.5 parts of white carbon; and 54 parts of water are mixed and finely pulverized by a wet pulverization method to obtain each 10% flowable formulation.

Formulation Example 52

Ten parts (10 parts) of any one of the present compounds 1 to 8 and 1 part of tebuconazole; 17.5 parts of a polyoxyethylene alkyl ether sulfate ammonium salt; 17.5 parts of white carbon; and 54 parts of water are mixed and finely pulverized by a wet pulverization method to obtain each 10% flowable formulation.

Formulation Example 53

Ten parts (10 parts) of any one of the present compounds 1 to 8 and 1 part of difenoconazole; 17.5 parts of a polyoxyethylene alkyl ether sulfate ammonium salt; 17.5 parts of white carbon; and 54 parts of water are mixed and finely pulverized by a wet pulverization method to obtain each 10% flowable formulation.

Formulation Example 54

Ten parts (10 parts) of any one of the present compounds 1 to 8 and 1 part of sedaxane; 17.5 parts of a polyoxyethylene alkyl ether sulfate ammonium salt; 17.5 parts of white carbon; and 54 parts of water are mixed and finely pulverized by a wet pulverization method to obtain each 10% flowable formulation.

Formulation Example 55

Ten parts (10 parts) of any one of the present compounds 1 to 8 and 1 part of penflufen; 17.5 parts of a polyoxyethylene alkyl ether sulfate ammonium salt; 17.5 parts of white carbon; and 54 parts of water are mixed and finely pulverized by a wet pulverization method to obtain each 10% flowable formulation.

Formulation Example 56

Ten parts (10 parts) of any one of the present compounds 1 to 8 and 1 part of fludioxonil; 17.5 parts of a polyoxyethylene alkyl ether sulfate ammonium salt; 17.5 parts of white carbon; and 54 parts of water are mixed and finely pulverized by a wet pulverization method to obtain each 10% flowable formulation.

Formulation Example 57

Ten parts (10 parts) of any one of the present compounds 1 to 8 and 1 part of ethaboxam; 17.5 parts of a polyoxyethylene alkyl ether sulfate ammonium salt; 17.5 parts of white carbon; and 54 parts of water are mixed and finely pulverized by a wet pulverization method to obtain each 10% flowable formulation.

Formulation Example 58

Ten parts (10 parts) of any one of the present compounds 1 to 8 and 1 part of tolclofos-methyl; 17.5 parts of a polyoxyethylene alkyl ether sulfate ammonium salt; 17.5 parts of white carbon; and 54 parts of water are mixed and finely pulverized by a wet pulverization method to obtain each 10% flowable formulation.

Formulation Example 59

Ten parts (10 parts) of any one of the present compounds 1 to 8 and 1 part of the present fungicidally active compound 5; 17.5 parts of a polyoxyethylene alkyl ether sulfate ammonium salt; 17.5 parts of white carbon; and 54 parts of water are mixed and finely pulverized by a wet pulverization method to obtain each 10% flowable formulation.

Next, examples of application of the inventive composition to plant seeds will be shown.

Application Example 1

Each flowable formulation produced in Formulation Example 45 to Formulation Example 59 is used for smear treatment in an amount of 200 ml per 100 kg of corn dried seeds using a rotary seed treatment machine (seed dresser, manufactured by Hans-Ulrich Hege GmbH) so as to obtain each treated seeds.

Application Example 2

Each flowable formulation produced in Formulation Example 45 to Formulation Example 59 is used for smear treatment in an amount of 50 ml per 10 kg of cotton dried seeds using a rotary seed treatment machine (seed dresser, manufactured by Hans-Ulrich Hege GmbH) so as to obtain each treated seeds.

Application Example 3

Each flowable formulation produced in Formulation Example 45 to Formulation Example 59 is used for smear treatment in an amount of 10 ml per 10 kg of soybean dried seeds using a rotary seed treatment machine (seed dresser, manufactured by Hans-Ulrich Hege GmbH) so as to obtain each treated seeds.

Application Example 4

Each flowable formulation produced in Formulation Example 45 to Formulation Example 59 is used for smear treatment in an amount of 100 ml per 10 kg of sugar beet dried seeds using a rotary seed treatment machine (seed dresser, manufactured by Hans-Ulrich Hege GmbH) so as to obtain each treated seeds.

Application Example 5

Each flowable formulation produced in Formulation Example 45 to Formulation Example 59 is used for smear treatment in an amount of 50 ml per 10 kg of oilseed rape dried seeds using a rotary seed treatment machine (seed dresser, manufactured by Hans-Ulrich Hege GmbH) so as to obtain each treated seeds.

Application Example 6

Each flowable formulation produced in Formulation Example 45 to Formulation Example 59 is used for smear treatment in an amount of 40 ml per 10 kg of wheat dried seeds using a rotary seed treatment machine (seed dresser, manufactured by Hans-Ulrich Hege GmbH) so as to obtain each treated seeds.

Application Example 7

Each flowable formulation produced in Formulation Example 45 to Formulation Example 59 is used for smear treatment in an amount of 200 ml per 100 kg of rice dried seeds using a rotary seed treatment machine (seed dresser, manufactured by Hans-Ulrich Hege GmbH) so as to obtain each treated seeds.

The following test examples show that the inventive composition promotes the growth of a plant.

Test Example 1

Test of Evaluation of Growth Promotion by *Nicotiana benthamiana* Hydroponics Under Low Temperature Stress (Test Plant)

*Nicotiana benthamiana*

(Cultivation Condition and Compound Treatment Method)

Two-fold diluted Murashige-and-Skoog medium (a medium containing 2.3 g of a mixture of salts for Murashige-and-Skoog medium (manufactured by Wako Pure Chemical Industries, Ltd.), 200 mg of myoinositol (manufactured by Sigma-Aldrich), 2 mg of nicotinic acid (manufactured by Wako Pure Chemical Industries, Ltd.), 2 mg of pyridoxine hydrochloride (manufactured by Wako Pure Chemical Industries, Ltd.), 20 mg of thiamine' hydrochloride (manufactured by Wako Pure Chemical Industries, Ltd.), 20 g of sucrose (manufactured by Wako Pure Chemical Industries, Ltd.) and 1 g of MES (manufactured by DOJINDO LABORATORIES) in 1 L of water, adjusted to pH 5.8)(5 µL) was dispensed onto a 96-well plastic plate, seeds of *Nicotiana benthamiana* were sown, and cultivated at 22° C. overnight. Thereafter, 45 µL of the above-described medium (containing 0.1% DMSO) containing the present condensed ring compound 1 and the present fungicidally active compound was further added to each well, to obtain 50 µL of a medium containing the present condensed ring compound 1 and any of the present fungicidally active compound in final concentrations shown in Table 2. It was cultivated for 7 days under conditions of an illuminance of 2000 lux, a temperature of 22° C. and a day length of 16 hours.

Separately, 45 µL of a medium prepared by adding DMSO at a volume ratio of 1/1000 to two-fold diluted Murashige-and-Skoog medium was added to give 50 µL of a medium, and seeds and seedlings of *Nicotiana benthamiana* were cultivated in the same manner, as a non-treated group.

(Cultivation Condition Under Low Temperature Stress)

The seedlings cultivated as described above were cultivated for 7 days under conditions of an illuminance of 2000 lux, a temperature of 1.5±1.0° C. and a day length of 16 hours, to effect low temperature stress treatment. Also the seedlings in the non-treated group were subjected to low temperature stress treatment in the same manner.

(Evaluation Method)

Seedlings of *Nicotiana benthamiana* subjected to low temperature stress treatment in a group treated with the inventive agrichemical composition and a non-treated group were cultivated for 3 days under conditions of an illuminance of 3000 lux, a temperature of 22° C. and a day length of 16 hours, and the seedlings before low temperature stress treatment and the seedlings 3 days after low temperature stress treatment were photographed by Scanalyzer HTS (manufactured by LemnaTec), and the area of green parts of leaves of seedlings was calculated. The relative leaf area was calculated according to the following calculation formula, the area of green parts in the non-treated group after low temperature stress treatment being 0% and the area of green parts directly before low temperature stress treatment being 100%. The results are shown in Table 2.

As a result of evaluation, in the group treated with the inventive composition, an apparent increase in the green leaf area was observed, thus, promotion of growth could be confirmed.

(Relative leaf area)=100×{(area of green parts of leaves of seedlings in composition-treated group 3 days after low temperature stress treatment)−(area of green parts of leaves of seedlings in non-treated group 3 days after low temperature stress treatment)}/(area of green parts of leaves of seedlings in non-treated group directly before low temperature stress treatment)      <Calculation formula>

TABLE 2

| Test compound | concentration (ppm) | relative leaf area (%) |
|---|---|---|
| Present condensed ring compound 1 + metalaxyl | 0 + 0.5 | 0 |
| Present condensed ring compound 1 + metalaxyl | 3 + 0.5 | 33.3 |
| Present condensed ring compound 1 + metalaxylM | 0 + 0.05 | 0 |
| Present condensed ring compound 1 + metalaxylM | 3 + 0.05 | 74.1 |
| Present condensed ring compound 1 + pyraclostrobin | 0 + 0.05 | 0 |
| Present condensed ring compound 1 + pyraclostrobin | 3 + 0.05 | 59.4 |
| Present condensed ring compound 1 + trifloxystrobin | 0 + 5 | 0 |
| Present condensed ring compound 1 + trifloxystrobin | 3 + 5 | 36.8 |
| Present condensed ring compound 1 + azoxystrobin | 0 + 0.01 | 0 |
| Present condensed ring compound 1 + azoxystrobin | 3 + 0.01 | 20.0 |
| Present condensed ring compound 1 + metconazole | 0 + 0.05 | 2.1 |
| Present condensed ring compound 1 + metconazole | 3 + 0.05 | 55.7 |
| Present condensed ring compound 1 + ipconazole | 0 + 0.5 | 0 |
| Present condensed ring compound 1 + ipconazole | 3 + 0.5 | 96.6 |
| Present condensed ring compound 1 + tebuconazole | 0 + 0.05 | 0 |
| Present condensed ring compound 1 + tebuconazole | 3 + 0.05 | 59.9 |
| Present condensed ring compound 1 + difenoconazole | 0 + 0.05 | 0 |
| Present condensed ring compound 1 + difenoconazole | 3 + 0.05 | 61.8 |
| Present condensed ring compound 1 + sedaxane | 0 + 0.5 | 0 |
| Present condensed ring compound 1 + sedaxane | 3 + 0.5 | 28.4 |
| Present condensed ring compound 1 + penflufen | 0 + 0.05 | 0 |
| Present condensed ring compound 1 + penflufen | 3 + 0.05 | 49.1 |
| Present condensed ring compound 1 + fludioxonil | 0 + 0.05 | 0 |
| Present condensed ring compound 1 + fludioxonil | 3 + 0.05 | 20.1 |
| Present condensed ring compound 1 + ethaboxam | 0 + 0.05 | 0 |
| Present condensed ring compound 1 + ethaboxam | 3 + 0.05 | 40.5 |
| Present condensed ring compound 1 + tolclofos-methyl | 0 + 0.05 | 0 |
| Present condensed ring compound 1 + tolclofos-methyl | 3 + 0.05 | 44.6 |
| Present condensed ring compound 1 + present fungicidally active compound 5 | 0 + 0.5 | 0 |
| Present condensed ring compound 1 + present fungicidally active compound 5 | 3 + 0.5 | 37.3 |

Test Example 2

Test of Evaluation of Promotion of Root Growth by Rice Hydroponics (Test Plant)
Rice (Cultivar: Nipponbare)
(Cultivation Condition and Compound Treatment Method)
A 0.01% DMSO-containing 4-fold diluted Hoagland hydroponics liquid (Hoagland and Arnon, California Agricultural Experiment Station 1950 Circular 347 pp. 34) containing the present condensed ring compound at a final concentration of 2 ppm and the present fungicidally active compound at a final concentration of 0.02 to 2 ppm is prepared.

Rice seeds are immersed in a 1% sodium hypochlorite aqueous solution for 10 minutes, then, immersed in a 70% ethanol solution, then, washed with distilled water to disinfect the seed surface. The disinfected seeds are immersed in the hydroponics liquid containing the test compound at the above-described concentration, and incubated for 3 days at a temperature of 28° C. under dark conditions to stimulate the germination of the seeds.

Then, 30 ml of a hydroponics liquid containing the test compound at the above-described concentration is dispensed into a plastic tube (20 mm in diameter × 113 mm in height) covered with a cardboard on the lateral surface for blocking a light. A float made of a foamed polystyrene board and a vinyl mesh was placed on the water surface of the hydroponics liquid, and the rice seeds obtained after the stimulation of germination are placed on the float floating on the water surface of the hydroponics liquid. The seeds are cultivated for 3 days under the conditions of an illuminance of 4000 lux at the top of the tube, a temperature of 26° C., a humidity of 50% and a day length of 16 hours.

<Evaluation Method>
The root length of the rice seedlings obtained after the cultivation is measured by using WinRHIZO system (manufactured by REGENT INSTRUMENTS), and the average value of the root length in the treated group is calculated.

As a result of evaluation, the root length in the treated group wherein the plants are treated with the inventive composition is expected to be much longer.

Test Example 3

Test of Evaluation of Promotion of Growth Under Low Temperature Stress by Treatment of Corn Seeds <Test Plants>
Corn (Cultivar: Kuromochi)
<Seed Treatment>
A blank slurry solution containing 10% (V/V) color coat red (Becker Underwood, Inc.), 10% (V/V) CF-Clear (Becker Underwood, Inc.) and 1.66% Maxim 4FS (Syngenta) is prepared.

A slurry solution is prepared by dissolving the present condensed ring compound and the present fungicidally active compound in the blank slurry solution such that the final treatment amount of the present condensed ring compound is 5 g or 50 g and the final treatment amount of the present fungicidally active compound is 0.05 g to 500 g, per 100 kg of corn seeds.

In a 50-ml centrifuge tube (manufactured by BD Japan) containing corn seeds, 0.35 ml of the slurry solution is added for each 14.4 g of the corn seeds and stirred until the slurry solution is dried, thereby coating the corn seeds. In addition, the seeds are coated with the blank slurry solution in the same manner, for a non-treated group.

<Cultivation Condition>

One of the treated corn seeds is sown in culture soil (AI-SAI) in each pot (55 mm in diameter×58 mm in height) and cultivated for 10 days under the conditions of a temperature of 27° G, an illuminance of 5,000 lux and a day length of 16 hours.

The grown seedlings are placed into an artificial weather control room (VHT-2-15P-NC2-S, manufactured by Nippon Medical & Chemical Instruments Co., Ltd) and cultivated for 4 days under conditions of a temperature of 2.5±1° C., a day length of 16 hours and an illuminance of 5000 lux.

Then, the grown plants are cultivated for 4 days under conditions of a temperature of 27° C., an illuminance of 5000 lux and a day length of 16 hours.

<Evaluation Method>

After cultivation, the fresh weight of the aerial part of the plants is measured, and the average weight per individual is calculated.

As a result of evaluation, an increase in the fresh weight of the aerial part is expected in the group treated with the inventive composition.

INDUSTRIAL APPLICABILITY OF THE INVENTION

According to the inventive method, it becomes possible to provide an excellent agrichemical composition promoting the growth of a plant, and the like.

By use of the agrichemical composition of the present invention, growth of a plant can be promoted effectively.

The invention claimed is:

1. An agrichemical composition comprising a compound represented by the formula (1):

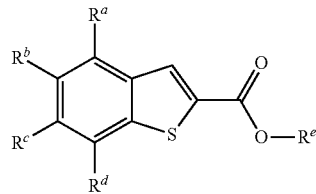

(1)

wherein, at least one of $R^a$, $R^b$, $R^c$ and $R^d$ represents a trifluoromethyl group and others represent a hydrogen atom, and $R^e$ represents a methyl group or an ethyl group, and at least one fungicidally active compound selected from the group consisting of Group (A):

Group (A): metalaxyl, metalaxyl-M, pyraclostrobin, trifloxystrobin, azoxystrobin, metconazole, ipconazole, tebuconazole, difenoconazole, sedaxane, penflufen, fludioxonil, ethaboxam, tolclofos-methyl, and compounds represented by the formula (4):

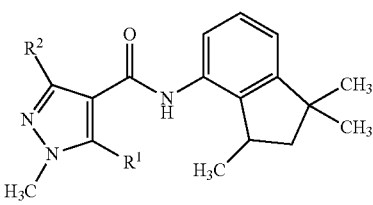

(4)

wherein, $R^1$ represents a hydrogen atom and $R^2$ represents a difluoromethyl group, and wherein the content ratio of the compound represented by the formula (1) to the at least one fungicidally active compound selected from the group consisting of Group (A) is 100:1 to 1:100 by weight.

2. The agrichemical composition according to claim 1, wherein the at least one fungicidally active compound selected from the group consisting of Group (A) is at least one fungicidally active compound selected from the group consisting of Group (B):

Group (B): metalaxyl and metalaxyl-M.

3. The agrichemical composition according to claim 1, wherein the at least one fungicidally active compound selected from the group consisting of Group (A) is at least one fungicidally active compound selected from the group consisting of Group (C):

Group (C): pyraclostrobin, trifloxystrobin, and azoxystrobin.

4. The agrichemical composition according to claim 1, wherein the at least one fungicidally active compound selected from the group consisting of Group (A) is at least one fungicidally active compound selected from the group consisting of Group (D):

Group (D): metconazole, ipconazole, tebuconazole, and difenoconazole.

5. The agrichemical composition according to claim 1, wherein the at least one fungicidally active compound selected from the group consisting of Group (A) is at least one fungicidally active compound selected from the group consisting of Group (E):

Group (E): sedaxane and penflufen.

6. The agrichemical composition according to claim 1, wherein the at least one fungicidally active compound selected from the group consisting of Group (A) is at least one fungicidally active compound selected from the group consisting of Group (F):

Group (F): fludioxonil, ethaboxam, tolclofos-methyl, and compounds represented by the formula (4):

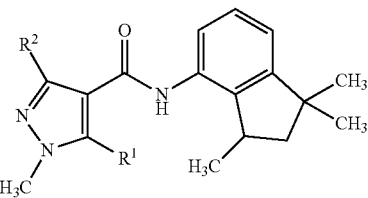

(4)

wherein, $R^1$ represents a hydrogen atom and $R^2$ represents a difluoromethyl group.

7. The agrichemical composition according to claim 1, wherein the compound represented by the formula (1) is methyl 5-(trifluoromethyl)benzo[b]thiophene-2-carboxylate.

8. A method of promoting the growth of a plant, having a step of applying an effective amount of the agrichemical composition according to claim 1 to a soil where the plant grows or the plant itself.

9. A method of promoting the growth of a plant, having a step of adhering an effective amount of the agrichemical composition according to claim 1 to a seed of the plant or impregnating a seed of the plant with an effective amount of the agrichemical composition and a step of sowing the plant seed.

10. A seed treating agent comprising the agrichemical composition according to claim 1.

11. A plant seed impregnated with an effective amount of the agrichemical composition according to claim 1 or comprising an effective amount of the agrichemical composition adhered.

12. The plant seed according to claim 11, wherein the kind of the plant seed is a seed of corn, cotton, soybean, sugar beet, rapeseed, wheat or rice.

* * * * *